(12) United States Patent
Rossi et al.

(10) Patent No.: US 12,156,887 B2
(45) Date of Patent: Dec. 3, 2024

(54) CHIMERIC RECEPTOR T CELL TREATMENT USING CHARACTERISTICS OF THE TUMOR MICROENVIRONMENT

(71) Applicant: Kite Pharma, Inc., Santa Monica, CA (US)

(72) Inventors: John M. Rossi, Santa Monica, CA (US); Adrian Bot, Santa Monica, CA (US)

(73) Assignee: Kite Pharma, Inc., Santa Monica, CA (US)

( * ) Notice: Subject to any disclaimer, the term of this patent is extended or adjusted under 35 U.S.C. 154(b) by 115 days.

(21) Appl. No.: 16/383,283

(22) Filed: Apr. 12, 2019

(65) Prior Publication Data

US 2019/0314410 A1    Oct. 17, 2019

Related U.S. Application Data

(60) Provisional application No. 62/831,946, filed on Apr. 10, 2019, provisional application No. 62/827,770, filed on Apr. 1, 2019, provisional application No. 62/656,825, filed on Apr. 12, 2018.

(51) Int. Cl.
*A61K 35/17*      (2015.01)
*A61P 35/00*      (2006.01)
*C07K 14/725*    (2006.01)
*G01N 33/574*    (2006.01)

(52) U.S. Cl.
CPC .............. *A61K 35/17* (2013.01); *A61P 35/00* (2018.01); *C07K 14/7051* (2013.01); *G01N 33/57484* (2013.01); *G01N 2800/52* (2013.01)

(58) Field of Classification Search
CPC ..... A61K 35/17; A61P 35/00; C07K 14/7051; G01N 33/57484
See application file for complete search history.

(56) References Cited

U.S. PATENT DOCUMENTS

| | | | |
|---|---|---|---|
| 5,728,388 A | 3/1998 | Terman | |
| 5,827,642 A | 10/1998 | Riddell et al. | |
| 6,040,177 A | 3/2000 | Riddell et al. | |
| 6,319,494 B1 | 11/2001 | Capon et al. | |
| 6,797,514 B2 | 9/2004 | Berenson et al. | |
| 6,867,041 B2 | 3/2005 | Berenson et al. | |
| 6,905,874 B2 | 6/2005 | Berenson et al. | |
| 7,741,465 B1 | 6/2010 | Eshhar et al. | |
| 8,481,271 B2* | 7/2013 | Galon | G01N 33/57492 435/7.1 |
| 10,340,030 B2* | 7/2019 | Bagaev | C12Q 1/6886 |
| 10,774,388 B2* | 9/2020 | Bedoya | A61P 43/00 |
| 2002/0006409 A1 | 1/2002 | Wood | |
| 2005/0239079 A1* | 10/2005 | Erlander | C12Q 1/6886 435/6.14 |
| 2013/0287748 A1 | 10/2013 | June et al. | |
| 2014/0050708 A1 | 2/2014 | Powell et al. | |
| 2014/0099309 A1 | 4/2014 | Powell, Jr. et al. | |
| 2014/0154228 A1 | 6/2014 | Volk et al. | |
| 2014/0227237 A1 | 8/2014 | June et al. | |
| 2014/0303034 A1* | 10/2014 | Gascoyne | G16B 25/10 506/9 |
| 2016/0363593 A1* | 12/2016 | Sebastiao | G01N 33/566 |
| 2017/0306416 A1 | 10/2017 | Bedoya et al. | |
| 2018/0100201 A1* | 4/2018 | Garraway | C12Q 1/6886 |
| 2019/0314410 A1 | 10/2019 | Rossi et al. | |
| 2019/0365836 A1* | 12/2019 | Galanis | A61K 35/768 |

FOREIGN PATENT DOCUMENTS

| | | | |
|---|---|---|---|
| WO | WO 2008/081035 | 7/2008 | |
| WO | WO 2012/079000 | 6/2012 | |
| WO | WO 2012/129514 | 9/2012 | |
| WO | 2016/057705 A1 | 4/2016 | |
| WO | WO-2016164731 A2 * | 10/2016 | ......... C07K 16/2866 |
| WO | WO 2018/013563 A1 | 1/2018 | |
| WO | WO 2018/064205 | 4/2018 | |
| WO | 2019/089858 A2 | 5/2019 | |

OTHER PUBLICATIONS

Ji et al. "An immune-active tumor microenvironment favors clinical response to ipilimumab", Cancer Immunol Immunother. Jul. 2012; 61(7):1019-31. (Year: 2012).*
Pont et al. "Microarray Gene Expression Analysis to Evaluate Cell Type Specific Expression of Targets Relevant for Immunotherapy of Hematological Malignancies", PLoS One. May 12, 2016;11(5):e0155165. (Year: 2016).*
Dennis et al. "Multiplexed Cancer Immune Response Analysis nCounter® PanCancer Immune Profiling Panel for Gene Expression", Retrieved from the Internet on Jun. 7, 2023 from http://www.biosystems.com.ar/archivos/folletos/228/pdf.pdf (2014) (Year: 2014).*
Caruso et al. "Tuning sensitivity of CAR to EGFR density limits recognition of normal tissue while maintaining potent anti-tumor activity", Cancer Res. Sep. 1, 2015; 75(17): 3505-3518 (Year: 2015).*
Original and English Translated Office Action received for counterpart Taiwanese Patent Application Serial No. 108112939 dated Mar. 12, 2020, 6 pages.
U.S. Appl. No. 62/262,143, Kite Pharma, Inc.
U.S. Appl. No. 62/167,750, Kite Pharma, Inc.
Cheson et al. "Revised response criteria for malignant lymphoma", Journal of Clinical Oncology, 25(5): 579-86 (2007).

(Continued)

*Primary Examiner* — Amy E Juedes
*Assistant Examiner* — Peter Johansen
(74) *Attorney, Agent, or Firm* — Arrigo, Lee, Guttman & Mouta-Bellum LLP; Carla Mouta-Bellum

(57) ABSTRACT

The disclosure provides methods of treating a malignancy comprising administering an effective dose of a chimeric receptor (e.g., CAR or TCR) genetically modified T cell immunotherapy. Some aspects of the disclosure relate to methods of characterizing the pre-infusion tumor microenvironment and determining an effective dose of a T cell immunotherapy.

6 Claims, 16 Drawing Sheets

Specification includes a Sequence Listing.

(56) References Cited

OTHER PUBLICATIONS

Cheson et al., "Recommendations for initial evaluation, staging, and response assessment of Hodgkin and non-Hodgkin lymphoma: the Lugano classification", Journal of Clinical Oncology, 32(27): 3059-3067 (2014).
Eshhar et al., "Tumor-specific T-bodies: towards clinical application", Cancer Immunol Immunotherapy, 45(3-4): 131-136 (1997).
Finney et al., "Chimeric receptors providing both primary and costimulatory signaling in T cells from a single gene product", Journal of Immunology, 161(6): 2791-2797 (1998).
Galon et al. "Towards the introduction of the 'immunoscore' in the classification of malignant tumours", J Pathol, 232:199-209 (2014).
Galon et al. "The continuum of cancer immunosurveillance: prognostic, predictive, and mechanistic signatures", Immunit,y 39:11-26 (2013).
Gross et al., "Therapeutic Potential of T Cell Chimeric Antigen Receptors (CARs) in Cancer Treatment: Counteracting Off-Tumor Toxicities for Safe Car T Cell Therapy", Annu. Rev. Pharmacol. Toxicol., 56: 59-83 (2016).
Kalos et al., "T cells with chimeric antigen receptors have potent antitumor effects and can establish memory in patients with advanced leukemia", Sci. Transl. Med., 3(95): 95ra73 (2011).
Krause et al., "Antigen-dependent CD28 Signaling Selectively Enhances Survival and Proliferation in Genetically Modified Activated Human Primary T Lymphocytes", J. Exp. Med., 188(4): 619-626 (1998).
Neelapu et al., "Axicabtagene ciloleucel CAR T-cell therapy in refractory large B- cell lymphoma", N. Engl. J. Med., 377:2531-2544 (2017).
Porter et al., "Chimeric antigen receptor-modified T cells in chronic lymphoid leukemia", N. Engl. J. Med., 365(8): 725-33 (2011).
Rimsza et al., "Loss of MHC class II gene and protein expression in diffuse large B cell lymphoma is related to decreased tumor immunosurveillance and poor patient survival: a follow-up study from the Leukemia and Lymphoma Molecular Profiling Project" Blood, 103: 4251-4258 (2004).
Song et al., "CD27 costimulation augments the survival and anti-tumor activity of redirected human T cells in vivo", Blood, 119(3): 696-706 (2012).
Haliodx, www.haliodx.com/clinical-research-services/immunosignr/ (2019).
Nanostring Technologies, Inc. www.nanostring.com/products/gene-expression-panels/hallmarks-cancer-gene-expression-panel-collection/pancancer-immune-profiling-panel (2019).
International Search Report and Written Opinion received in PCT Application Serial No. PCT/US2019/27332 dated Aug. 2, 2019, 13 pages.
Weijtens et al., "Functional balance between T cell chimeric receptor density and tumor associated antigen density: CTL mediated cytolysis and lymphokine production", Gene Therapy, 2000, vol. 7, pp. 35-42.
Galon et al., "Characterization of anti-CD19 chimeric antigen receptor (CAR) T cell-mediated tumor microenvironment immune gene profile in a multicenter trial (ZUMA-1) with axicabtagene ciloleucel (axi-cel, KTE-C19)", Journal of Clinical Oncology, 2017 35:15, p. 3025.
HalioDX: "Immunosign® Try our immune gene expression signatures toinvestigate immune response", web.archive.org., Mar. 24, 2018.
Rossi et al., "Characteristics of the pretreatment tumor microenvironment may influence clinical response in patients with refractory large B cell lymphoma treated with axicabtagene ciloleucel (axi-cel) in the pivotal ZUMA-1", Cancer Research Conference. 2018, vol. 78, No. 13.
Kümpers et al., "Immune Cell Infiltration of the Primary Tumor, Not PD-L1 Status, is Associated With Improved Response to Check-point Inhibition in Metastatic Melanoma", Frontiers medicine, Mar. 2019, vol. 6, pp. 1-11.
Taiwan Office Action and English translation of Search Report issued Jan. 17, 2022 in connection with Taiwan Application No. 109134631, 6 pages.
English translation of Taiwan Office Action issued Jan. 17, 2022 in connection with Taiwan Application No. 109134631, 3 pages, which was previously submitted in the IDS of Feb. 24, 2022.
Canadian Patent Application No. 3,096,401: Examination Report dated Jul. 27, 2022, 5 pages.
Australian Patent Application No. 2019252944: Second Examination Report Report dated Sep. 23, 2022, 3 pages.
Galanina et al., "Emerging role of checkpoint blockade therapy in lymphoma", Therapeutic Advances in Hematology, vol. 8/2, 2017, pp. 81-90.
Australian Notice of Acceptance issued Nov. 24, 2022 in connection with Foreign Counterpart Australian Application No. 2019252944, 3 pages.
Japanese Office Action with English language translation issued Apr. 4, 2023 in connection with foreign counterpart Japanese Application No. 2020-555213, 14 pages.
Israel Office Action issued Apr. 17, 2023 in connection with foreign counterpart Israel Application No. 277977, 4 pages.
Office Action with English language translation issued Jul. 12, 2023 in connection with foreign counterpart Taiwan Application No. 111139861 (8 pages).
1 Canadian Patent Application No. 3,096,401: Office Action dated Sep. 13, 2023, 5 pages.
Office Action issued Jun. 6, 2024 in counterpart Chinese Pat. Appln. No. 201980025411.7, with English translation and pending rejected claims (12 pages).
Notice of Allowance for counterpart Israel Application No. 277977, Nov. 27, 2023, 3 pages.
Office Action dated Dec. 25, 2023 for counterpart Chinese Patent Application No. 201980025411.7: (13 pages).
Office Action issued May 15, 2024 in counterpart ROC (Taiwan) Pat. Appln. No. 111139861 Office Action (13 pages).
Office Action issued Jan. 25, 2024 in counterpart Israeli Pat. Appln. No. 310416 Office Action (5 pages).
Japanese Patent Application No. 2020-555213: Office Action dated Oct. 17, 2023, 9 pages.
Office Action issued Aug. 22, 2024 in counterpart Chinese Pat. Appln. No. 201980025411.7, with English translation and pending rejected claims ( 15 pages).

* cited by examiner

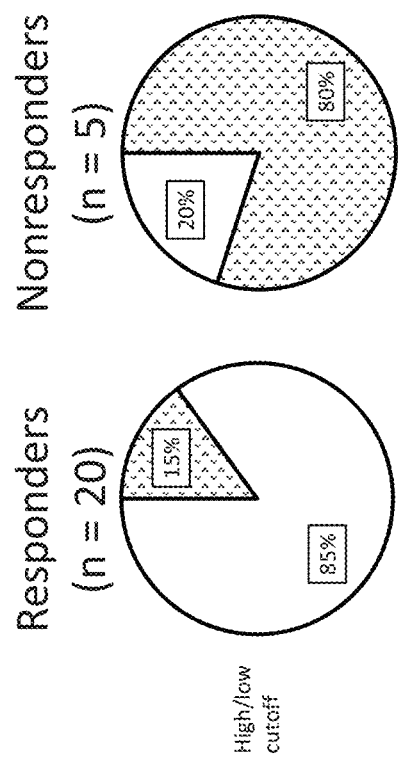
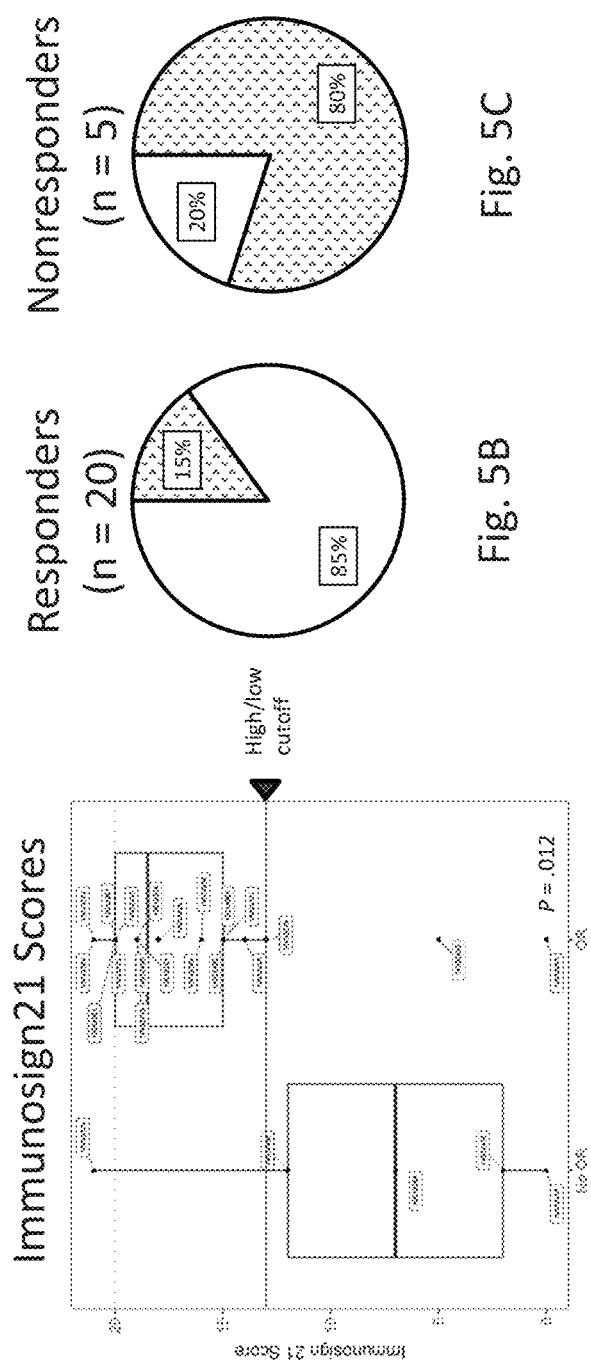
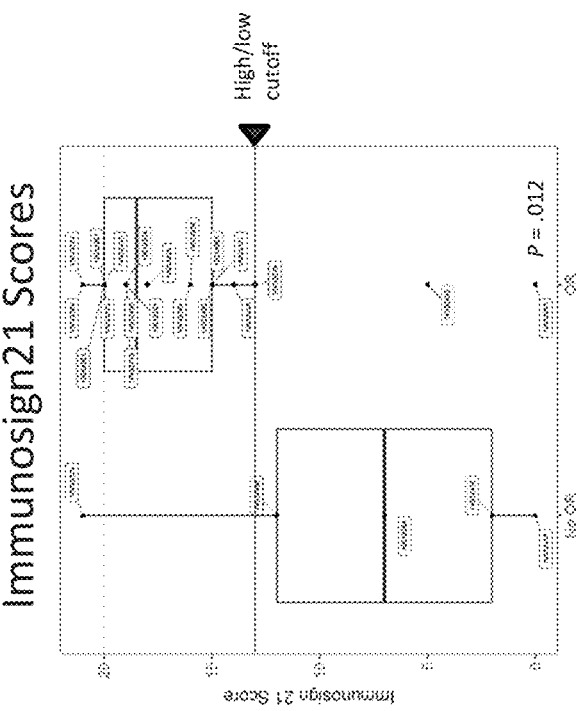
Fig. 5A
Fig. 5B
Fig. 5C

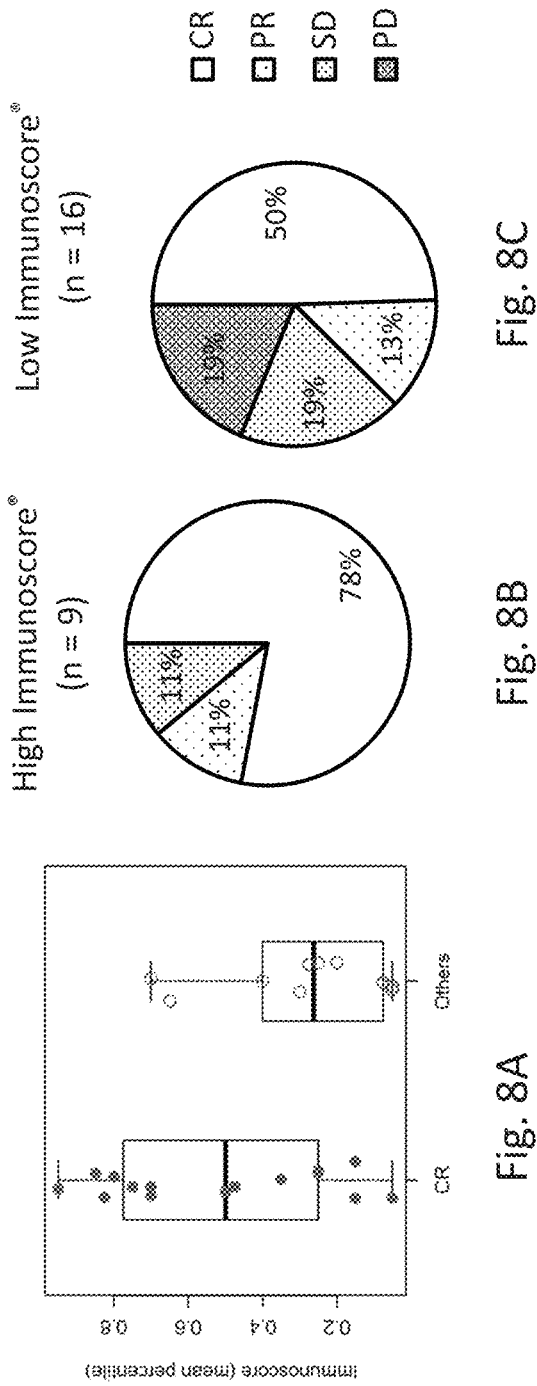

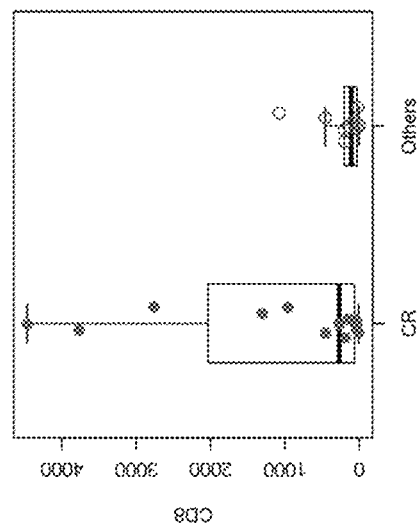
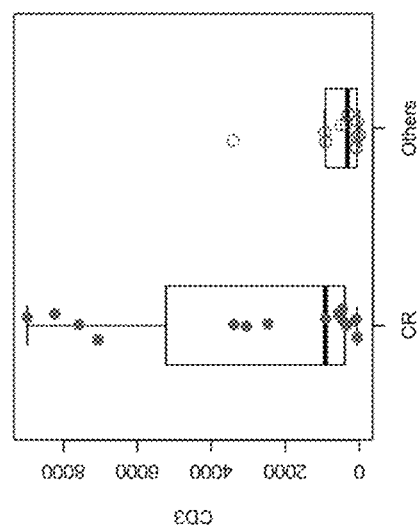
Fig. 9A
Fig. 9B

SEQUENCE LISTING

```
<160> NUMBER OF SEQ ID NOS: 2

<210> SEQ ID NO 1
<211> LENGTH: 18
<212> TYPE: PRT
<213> ORGANISM: Artificial Sequence
<220> FEATURE:
<223> OTHER INFORMATION: Linker Sequence

<400> SEQUENCE: 1

Gly Ser Thr Ser Gly Ser Gly Lys Pro Gly Ser Gly Glu Gly Ser Thr
1               5                   10                  15

Lys Gly

<210> SEQ ID NO 2
<211> LENGTH: 5
<212> TYPE: PRT
<213> ORGANISM: artificial sequence
<220> FEATURE:
<223> OTHER INFORMATION: linker peptide

<400> SEQUENCE: 2

Gly Gly Gly Gly Ser
1               5
```

CHIMERIC RECEPTOR T CELL TREATMENT USING CHARACTERISTICS OF THE TUMOR MICROENVIRONMENT

CROSS REFERENCE TO RELATED APPLICATIONS

This application claims priority to U.S. Provisional Patent Application No. 62/656,825 filed Apr. 12, 2018; to U.S. Provisional Patent Application No. 62/827,770 filed Apr. 1, 2019; and to U.S. Provisional Patent Application No. 62/831,946 filed Apr. 10, 2019, each of which are incorporated by reference herein in their entirety.

SEQUENCE LISTING

This application contains a Sequence Listing which has been submitted electronically in ASCII format and is hereby incorporated by reference in its entirety. Said ASCII copy, created on Apr. 11, 2019, is named K-1065_01_SL.txt and is 8 kilobytes in size.

BACKGROUND

Human cancers are by their nature comprised of normal cells that have undergone a genetic or epigenetic conversion to become abnormal cancer cells. In doing so, cancer cells begin to express proteins and other antigens that are distinct from those expressed by normal cells. These aberrant tumor antigens can be used by the body's innate immune system to specifically target and kill cancer cells. However, cancer cells employ various mechanisms to prevent immune cells, such as T and B lymphocytes, from successfully targeting cancer cells.

Human T cell therapies rely on enriched or modified human T cells to target and kill cancer cells in a patient. To increase the ability of T cells to target and kill a particular cancer cell, methods have been developed to engineer T cells to express constructs which direct T cells to a particular target cancer cell. Chimeric antigen receptors (CARs) and engineered T cell receptors (TCRs), which comprise binding domains capable of interacting with a particular tumor antigen, allow T cells to target and kill cancer cells that express the particular tumor antigen.

SUMMARY

Tumor microenvironment (TME) characteristics prior to CAR T cell infusion may influence clinical outcomes. The present disclosure provides methods of assessing the TME using an immune-related gene expression signature of the TME and/or intratumoral T cell density, to associate with outcomes.

Each of the aspects and embodiments described below can be combined, unless the context clearly indicates otherwise.

In one aspect, the present disclosure provides a method of treating a malignancy in a patient comprising: (a) analyzing a tumor biopsy from the patient to characterize the tumor microenvironment; and (b) administering an effective dose of T cells comprising one or more chimeric receptors to the patient, wherein the effective dose is determined using the characteristics of the tumor microenvironment.

In some embodiments, the tumor microenvironment is characterized using gene expression profiling. In some embodiments, the tumor microenvironment is characterized based on intratumoral T cell density. In some embodiments, the tumor microenvironment is characterized using gene expression profiling and intratumoral T cell density.

In some embodiments, the gene expression profiling comprises determining the expression level of a specified panel of genes. In some embodiments, the panel comprises CD3G, STAT4, CD3E, CD3D, GZMK, GZMM, PRF1, CD8A, ICOS, CXCL10, STAT1, IL15, CCR2, CCL2, IRF1, TBX21, GZMA, CXCR3, GZMB, CD69, CXCL11, and a combination thereof. In some embodiments, the panel comprises CTLA4, GZMH, CD8A, PDCD1, CD3G, IRF1, CX3CL1, TNFRSF9, CD3E, GZMA, CXCL10, TSLP, REN, GZMB, TNFRSF18, CCL2, GZMK, CXCL11, CD69, CD247, CCL5, STAT4, CD274, GNLY, ITGAE, LAG3, IL15, LTK, PRF1, CD3D, PF4, TBX21, ICOS, CXCL9, IFNG, VEGFA, STAT1, GZMM, CXCL13, CXCR3, CCR2, IL17A, PROM1, and a combination thereof. In some embodiments, the panel comprises the PanCancer Immune Profiling Panel.

In some embodiments, the method comprises determining the expression level of one or more genes selected from CD3G, STAT4, CD3E, CD3D, GZMK, GZMM, PRF1, CD8A, ICOS, CXCL10, STAT1, IL15, CCR2, CCL2, IRF1, TBX21, GZMA, CXCR3, GZMB, CD69, CXCL11, and a combination thereof.

In some embodiments, the method comprises determining the expression level of one or more genes selected from CTLA4, GZMH, CD8A, PDCD1, CD3G, IRF1, CX3CL1, TNFRSF9, CD3E, GZMA, CXCL10, TSLP, REN, GZMB, TNFRSF18, CCL2, GZMK, CXCL11, CD69, CD247, CCL5, STAT4, CD274, GNLY, ITGAE, LAG3, IL15, LTK, PRF1, CD3D, PF4, TBX21, ICOS, CXCL9, IFNG, VEGFA, STAT1, GZMM, CXCL13, CXCR3, CCR2, IL17A, PROM1, and a combination thereof.

In some embodiments, the method comprises determining the expression level of genes selected from the PanCancer Immune Profiling Panel.

In some embodiments, the method comprises determining the expression level of B cell markers. In some embodiments, the B cell markers are selected from BLK, CD19, CR2, MS4A1, TNFRSF17, and a combination thereof.

In some embodiments, the method comprises determining the expression level of T cell markers. In some embodiments, the T cell markers are selected from CD2, CD2E, CD3G, CD6, and a combination thereof.

In some embodiments, the method comprises determining the expression level of a specified panel of genes comprises genes associated with innate immune response. In some embodiments, the specified panel of genes comprises markers of cytotoxic cells, dendritic cells, macrophages, granulocytes, and combinations thereof.

In some embodiments, the specified panel of genes comprises genes selected from CD8, BLC2, and a combination thereof.

In some embodiments, the specified panel of genes comprises genes selected from CCL12, CCL17, and a combination thereof.

In some embodiments, the specified panel of genes comprises genes selected from APOE, CCL7, and a combination thereof.

In some embodiments, the specified panel of genes comprises genes selected from CMA1, CSF3R, and a combination thereof.

In some embodiments, the method comprises determining the expression level of one or more genes selected from CTLA4, CD3g, CD3e, CD27, SH2B2, ICOSL, and a combination thereof.

In some embodiments, the method comprises determining the expression level of one or more genes selected from CD27, SH2B2, ICOSLG, HLA-DQA1, HLA-DQB1, MAGEB2, PRAME, MAGEA1, IL22RA1, SSX1, CCL20, NEFL, C9, GZMM, KIR Act Subgroup 2, HLA-DOB, and a combination thereof.

In some embodiments, the method comprises determining the expression level of one or more genes selected from CD27, SH2B2, ICOSLG, and a combination thereof.

In some embodiments, the method comprises determining the expression level of one or more genes selected from HLA-DQA1, HLA-DQB1, MAGEB2, PRAME, MAGEA1, IL22RA1, SSX1, CCL20, NEFL, C9, GZMM, KIR Act Subgroup 2, HLA-DOB, and a combination thereof.

In some embodiments, the method comprises determining the density of T cells in the tissue microenvironment (i.e., intratumoral T cell density), such as by immunohistochemical staining of a tumor biopsy. In some embodiments, the method comprises determining the density of CD3+ and/or CD8+ T cells in the tissue microenvironment.

In some embodiments, the method comprises determining an immune score based on the gene expression profile. In some embodiments, the method comprises determining an immune score based on the intratumoral T cell density. In some embodiments, the method comprises modulating the total dose of CAR-T cells using the immune score. In some embodiments, the method comprises providing an immunomodulatory compound or intervention to increase the immune score prior to CAR-T cell administration.

In some embodiments, the effective dose comprises at least $1\times10^6$ CAR-positive viable T cells per kg body weight.

In some embodiments, the chimeric receptor targets a tumor antigen. In some embodiments, the chimeric receptor targets a tumor antigen selected from a tumor-associated surface antigen, such as 5T4, alphafetoprotein (AFP), B7-1 (CD80), B7-2 (CD86), BCMA, B-human chorionic gonadotropin, CA-125, carcinoembryonic antigen (CEA), carcinoembryonic antigen (CEA), CD123, CD133, CD138, CD19, CD20, CD22, CD23, CD24, CD25, CD30, CD33, CD34, CD4, CD40, CD44, CD56, CD8, CLL-1, c-Met, CMV-specific antigen, CS-1, CSPG4, CTLA-4, DLL3, disialoganglioside GD2, ductal-epithelial mucine, EBV-specific antigen, EGFR variant III (EGFRvIII), ELF2M, endoglin, ephrin B2, epidermal growth factor receptor (EGFR), epithelial cell adhesion molecule (EpCAM), epithelial tumor antigen, ErbB2 (HER2/neu), fibroblast associated protein (fap), FLT3, folate binding protein, GD2, GD3, glioma-associated antigen, glycosphingolipids, gp36, HBV-specific antigen, HCV-specific antigen, HER1-HER2, HER2-HER3 in combination, HERV-K, high molecular weight-melanoma associated antigen (HMW-MAA), HIV-1 envelope glycoprotein gp41, HPV-specific antigen, human telomerase reverse transcriptase, IGFI receptor, IGF-II, IL-11Ralpha, IL-13R-a2, Influenza Virus-specific antigen; CD38, insulin growth factor (IGFI)-1, intestinal carboxyl esterase, kappa chain, LAGA-1a, lambda chain, Lassa Virus-specific antigen, lectin-reactive AFP, lineage-specific or tissue specific antigen such as CD3, MAGE, MAGE-A1, major histocompatibility complex (MHC) molecule, major histocompatibility complex (MHC) molecule presenting a tumor-specific peptide epitope, M-CSF, melanoma-associated antigen, mesothelin, mesothelin, MN-CA IX, MUC-1, mut hsp70-2, mutated p53, mutated p53, mutated ras, neutrophil elastase, NKG2D, Nkp30, NY-ESO-1, p53, PAP, prostase, prostate specific antigen (PSA), prostate-carcinoma tumor antigen-1 (PCTA-1), prostate-specific antigen protein, STEAP1, STEAP2, PSMA, RAGE-1, ROR1, RU1, RU2 (AS), surface adhesion molecule, surviving and telomerase, TAG-72, the extra domain A (EDA) and extra domain B (EDB) of fibronectin and the A1 domain of tenascin-C (TnC A1), thyroglobulin, tumor stromal antigens, vascular endothelial growth factor receptor-2 (VEGFR2), virus-specific surface antigen such as an HIV-specific antigen (such as HIV gp120), as well as any derivate or variant of these surface markers.

In some embodiments, the chimeric receptor specifically targets CD19.

In some embodiments, the chimeric receptor is a chimeric antigen receptor (CAR). In some embodiments, the chimeric receptor is a T cell receptor (TCR).

In some embodiments, the malignancy is a solid tumor, sarcoma, carcinoma, lymphoma, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), chronic or acute leukemia, acute myeloid leukemia, chronic myeloid leukemia, acute lymphoblastic leukemia (ALL) (including non T cell ALL), chronic lymphocytic leukemia (CLL), T-cell lymphoma, one or more of B-cell acute lymphoid leukemia ("BALL"), T-cell acute lymphoid leukemia ("TALL"), acute lymphoid leukemia (ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, myelodysplasia and myelodysplastic syndrome, plasmablastic lymphoma, plasmacytoid dendritic cell neoplasm, Waldenstrom macroglobulinemia, a plasma cell proliferative disorder (e.g., asymptomatic myeloma (smoldering multiple myeloma or indolent myeloma), monoclonal gammapathy of undetermined significance (MGUS), plasmacytomas (e.g., plasma cell dyscrasia, solitary myeloma, solitary plasmacytoma, extramedullary plasmacytoma, and multiple plasmacytoma), systemic amyloid light chain amyloidosis, POEMS syndrome (also known as Crow-Fukase syndrome, Takatsuki disease, and PEP syndrome), or a combination thereof.

In some embodiments, the malignancy is diffuse large B-cell lymphoma (DLBCL), primary mediastinal large B-cell lymphoma, high grade B-cell lymphoma, non-Hodgkin lymphoma, metastatic melanoma, transformed follicular lymphoma, follicular lymphoma, mantle cell lymphoma, and multiple myeloma.

In some embodiments, the effective dose is optimized to increase likelihood of patient responding to treatment.

In some embodiments, the tumor biopsy is obtained from the patient prior to treatment with a chimeric receptor therapy.

In one aspect, the present disclosure comprises a method of determining whether a patient will respond to chimeric receptor treatment comprising: (a) analyzing a tumor biopsy from the patient to characterize the tumor microenvironment using a gene expression profile; (b) determining an immune score based on the gene expression profile; and (c) determining if the patient will respond to chimeric receptor treatment based on the immune score.

In one aspect, the present disclosure comprises a method of determining whether a patient will respond to chimeric receptor treatment comprising: (a) analyzing a tumor biopsy from the patient to characterize the tumor microenvironment by quantifying the intratumoral density of T cells (e.g., CD3+ and/or CD8+ T cells); (b) determining an immune score based on the intratumoral T cell density; and (c) determining if the patient will respond to chimeric receptor treatment based on the immune score.

In one aspect, the present disclosure provides a method of treating a malignancy in a patient comprising: (a) analyzing a tumor biopsy from the patient prior to chimeric receptor treatment to characterize the tumor microenvironment; (b) determining if the patient will respond to chimeric receptor treatment based on the characteristics of the tumor microenvironment; and (c) administering an effective dose of T cells comprising one or more chimeric receptors to the patient, wherein the effective dose is determined using the characteristics of the tumor microenvironment.

In some embodiments, the method further comprises determining whether additional therapies will improve clinical efficacy using characteristics of the tumor microenvironment. In some embodiments, chimeric receptor therapy is administered with additional therapies. In some embodiments, the additional therapy is administered in combination with the chimeric receptor therapy. In some embodiments, the additional therapy is administered before or after the chimeric receptor therapy.

In some embodiments, the method further comprises administering a cytokine therapy. In some embodiments, the cytokine therapy is IL-2 or IL-15.

In some embodiments, the method further comprises administering stimulating antibody. In some embodiments, the stimulating antibody is anti-41BB or OX-40.

In some embodiments, the method further comprises administering a checkpoint blockade therapy. In some embodiments, the checkpoint blockade therapy comprises CTLA4 or PD-1.

In some embodiments, the method further comprises administering an innate immune stimulator. In some embodiments, the innate immune stimulator comprises TLR or STING agonists.

In some embodiments, the gene expression profiling comprises determining the expression level of proliferative markers, inflammatory markers, immune modulating markers, effectors, and/or chemokines. In some embodiments, the method comprises determining the expression level of one or more genes selected from the IL-6, CRP, SAA, IL-5, Ferritin, IL-1Ra, IL-2Rα, and a combination thereof. In some embodiments, the method comprises determining the expression level of one or more genes selected from GM-CSF, IFN-γ, IL-10 and a combination thereof. In some embodiments, the method comprises determining the expression level of one or more genes selected from IL-8, IP-10, MCP-1, and a combination thereof. In some embodiments, the method comprises determining the expression level of Granzyme B. In some embodiments, the method comprises determining the expression level of CD3c, CD28, and CTLA4. In some embodiments, the method comprises determining the expression level of MX1, ISG15, and MYD88. In some embodiments, the method comprises determining the expression level of CD19, CD79B, and PAX5. In some embodiments, the method comprises determining the expression level of PD-L1 and/or CD19. In some embodiments, the tumor biopsy is obtained prior to treatment with CAR T cell therapy. In some embodiments, the tumor biopsy is obtained after treatment with CAR T cell therapy. In some embodiments, the method comprises obtaining a tumor biopsy prior to treatment with CAR T cell therapy and obtaining a tumor biopsy after treatment with CAR T cell therapy. In some embodiments, the tumor biopsy is obtained 7 days, 14 days, 21 days or 28 days after treatment with CAR T cell therapy.

BRIEF DESCRIPTION OF THE DRAWINGS

The drawings are for illustration purposes only, not for limitation.

FIG. 5A shows association between Immunosign®21 score and clinical outcome performed on samples from 25 patients treated with axicabtagene ciloleucel (axi-cel) with a minimum follow-up of 9 months. One patient subsequently converted from a "nonresponder" to "responder" at 12 months follow-up. FIG. 5B shows the proportion of patients who responded to axi-cel treatment with high and low baseline Immunosign®21 scores. FIG. 5C shows the proportion of patients who did not respond to axi-cel treatment with high and low baseline Immunosign®21 score. The high/low Immunosign®21 score cut off was defined as the $25^{th}$ percentile of the observed scores among samples. Stippling in FIGS. 5B and 5C indicates low Immunosign®21 score.

FIG. 8A shows association between mean percentile Immunoscore® and clinical outcome performed on samples from treated patients. FIG. 8B shows the proportion of clinical outcomes observed among patients who had a high baseline Immunoscore®. FIG. 8C shows the proportion of clinical outcomes observed among patients who had a low baseline Immunoscore®. The high/low Immunosign®21 score cut off was defined as median of the observed scores among samples. CR: complete response; PR: partial response; SD: stable disease; PD: progressive disease.

FIGS. 9A and 9B show the density of CD3+ cells and CD8+ cells, respectively, among complete responders and patients who exhibited other than complete response in baseline biopsy sections from treated patients.

DETAILED DESCRIPTION

Figure 1:
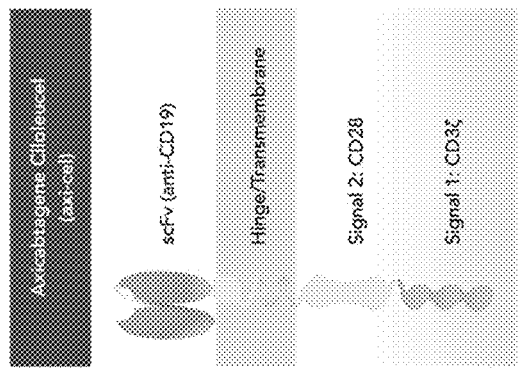
FIG. 1 shows a schematic representation of a chimeric antigen receptor (CAR) construct configuration.

The present disclosure relates to methods of treating a malignancy in a patient using characteristics of the tumor microenvironment of a patient biopsy. The present disclosure is based in part on the surprising discovery that characteristics of the tumor microenvironment of patient biopsies obtained prior to chimeric receptor treatment can be used to predict clinical outcomes. As described herein, the tumor microenvironment profile of prior to chimeric receptor treatment used to determine the effective dose to influence clinical outcomes of chimeric receptor (e.g., CAR or TCR) T cell therapy.

Definitions

In order for the present invention to be more readily understood, certain terms are first defined below. Additional definitions for the following terms and other terms are set forth throughout the Specification.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

The term "and/or" where used herein is to be taken as specific disclosure of each of the two specified features or components with or without the other. Thus, the term "and/or" as used in a phrase such as "A and/or B" herein is intended to include A and B; A or B; A (alone); and B (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The terms "e.g.," and "i.e." as used herein, are used merely by way of example, without limitation intended, and should not be construed as referring only those items explicitly enumerated in the specification.

The terms "or more", "at least", "more than", and the like, e.g., "at least one" are understood to include but not be limited to at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more than the stated value. Also included is any greater number or fraction in between.

Conversely, the term "no more than" includes each value less than the stated value. For example, "no more than 100 nucleotides" includes 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, and 0 nucleotides. Also included is any lesser number or fraction in between.

The terms "plurality", "at least two", "two or more", "at least second", and the like, are understood to include but not limited to at least 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more. Also included is any greater number or fraction in between.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. It is understood that wherever aspects are described herein with the language "comprising," otherwise analogous aspects described in terms of "consisting of" and/or "consisting essentially of" are also provided.

Unless specifically stated or evident from context, as used herein, the term "about" refers to a value or composition that is within an acceptable error range for the particular value or composition as determined by one of ordinary skill in the art, which will depend in part on how the value or composition is measured or determined, i.e., the limitations of the measurement system. For example, "about" or "approximately" can mean within one or more than one standard deviation per the practice in the art. "About" or "approximately" can mean a range of up to 10% (i.e., ±10%). Thus, "about" can be understood to be within 10%, 9%, 8%, 7%, 6%, 5%, 4%, 3%, 2%, 1%, 0.5%, 0.1%, 0.05%, 0.01%, or 0.001% greater or less than the stated value. For example, about 5 mg can include any amount between 4.5 mg and 5.5 mg. Furthermore, particularly with respect to biological systems or processes, the terms can mean up to an order of magnitude or up to 5-fold of a value. When particular values or compositions are provided in the instant disclosure, unless otherwise stated, the meaning of "about" or "approximately" should be assumed to be within an acceptable error range for that particular value or composition.

As described herein, any concentration range, percentage range, ratio range or integer range is to be understood to be inclusive of the value of any integer within the recited range and, when appropriate, fractions thereof (such as one-tenth and one-hundredth of an integer), unless otherwise indicated.

Units, prefixes, and symbols used herein are provided using their Système International de Unites (SI) accepted form. Numeric ranges are inclusive of the numbers defining the range.

Unless defined otherwise, all technical and scientific terms used herein have the same meaning as commonly understood by one of ordinary skill in the art to which this disclosure is related. For example, Juo, "The Concise Dictionary of Biomedicine and Molecular Biology", 2nd ed., (2001), CRC Press; "The Dictionary of Cell & Molecular Biology", 5th ed., (2013), Academic Press; and "The Oxford Dictionary Of Biochemistry And Molecular Biology", Cammack et al. eds., 2nd ed, (2006), Oxford University Press, provide those of skill in the art with a general dictionary for many of the terms used in this disclosure.

"Administering" refers to the physical introduction of an agent to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

The term "antibody" (Ab) includes, without limitation, a glycoprotein immunoglobulin which binds specifically to an antigen. In general, and antibody can comprise at least two heavy (H) chains and two light (L) chains interconnected by disulfide bonds, or an antigen-binding molecule thereof. Each H chain comprises a heavy chain variable region (abbreviated herein as VH) and a heavy chain constant region. The heavy chain constant region comprises three constant domains, CH1, CH2 and CH3. Each light chain comprises a light chain variable region (abbreviated herein as VL) and a light chain constant region. The light chain constant region is comprises one constant domain, CL. The VH and VL regions can be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the Abs may mediate the binding of the immunoglobulin to host tissues or factors, including various cells of the immune system (e.g., effector cells) and the first component (C1q) of the classical complement system.

Antibodies can include, for example, monoclonal antibodies, recombinantly produced antibodies, monospecific antibodies, multispecific antibodies (including bispecific antibodies), human antibodies, engineered antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, antibody fusions (sometimes referred to herein as "antibody conjugates"), heteroconjugate antibodies, single domain antibodies, monovalent antibodies, single chain antibodies or single-chain Fvs (scFv), camelized antibodies, affybodies, Fab fragments, F(ab')2 fragments, disulfide-linked Fvs (sdFv), anti-idiotypic (anti-Id) antibodies (including, e.g., anti-anti-Id antibodies), minibodies, domain antibodies, synthetic antibodies (sometimes referred to herein as "antibody mimetics"), and antigen-binding fragments of any of the above. In some embodiments, antibodies described herein refer to polyclonal antibody populations.

An "antigen binding molecule," "antigen binding portion," or "antibody fragment" refers to any molecule that comprises the antigen binding parts (e.g., CDRs) of the antibody from which the molecule is derived. An antigen binding molecule can include the antigenic complementarity determining regions (CDRs). Examples of antibody fragments include, but are not limited to, Fab, Fab', F(ab')2, and Fv fragments, dAb, linear antibodies, scFv antibodies, and multispecific antibodies formed from antigen binding molecules. Peptibodies (i.e., Fc fusion molecules comprising peptide binding domains) are another example of suitable antigen binding molecules. In some embodiments, the antigen binding molecule binds to an antigen on a tumor cell. In some embodiments, the antigen binding molecule binds to an antigen on a cell involved in a hyperproliferative disease or to a viral or bacterial antigen. In some embodiments, the antigen binding molecule binds to CD19. In further embodiments, the antigen binding molecule is an antibody fragment that specifically binds to the antigen, including one or more of the complementarity determining regions (CDRs) thereof. In further embodiments, the antigen binding molecule is a single chain variable fragment (scFv). In some embodiments, the antigen binding molecule comprises or consists of avimers.

An "antigen" refers to any molecule that provokes an immune response or is capable of being bound by an antibody or an antigen binding molecule. The immune response may involve either antibody production, or the activation of specific immunologically-competent cells, or both. A person of skill in the art would readily understand that any macromolecule, including virtually all proteins or peptides, can serve as an antigen. An antigen can be endogenously expressed, i.e. expressed by genomic DNA, or can be recombinantly expressed. An antigen can be specific to a certain tissue, such as a cancer cell, or it can be broadly expressed. In addition, fragments of larger molecules can act as antigens. In some embodiments, antigens are tumor antigens.

The term "neutralizing" refers to an antigen binding molecule, scFv, antibody, or a fragment thereof, which binds to a ligand and prevents or reduces the biological effect of that ligand. In some embodiments, the antigen binding molecule, scFv, antibody, or a fragment thereof, directly blocking a binding site on the ligand or otherwise alters the ligand's ability to bind through indirect means (such as structural or energetic alterations in the ligand). In some embodiments, the antigen binding molecule, scFv, antibody, or a fragment thereof prevents the protein to which it is bound from performing a biological function.

The term "autologous" refers to any material derived from the same individual to which it is later to be re-introduced.

For example, the engineered autologous cell therapy (eACT™) method described herein involves collection of lymphocytes from a patient, which are then engineered to express, e.g., a CAR construct, and then administered back to the same patient.

The term "allogeneic" refers to any material derived from one individual which is then introduced to another individual of the same species, e.g., allogeneic T cell transplantation.

The terms "transduction" and "transduced" refer to the process whereby foreign DNA is introduced into a cell via viral vector (see Jones et al., "Genetics: principles and analysis," Boston: Jones & Bartlett Publ. (1998)). In some embodiments, the vector is a retroviral vector, a DNA vector, a RNA vector, an adenoviral vector, a baculoviral vector, an Epstein Barr viral vector, a papovaviral vector, a vaccinia viral vector, a herpes simplex viral vector, an adenovirus associated vector, a lentiviral vector, or any combination thereof.

A "cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" can include a tumor. Examples of cancers that can be treated by the methods disclosed herein include, but are not limited to, cancers of the immune system including lymphoma, leukemia, myeloma, and other leukocyte malignancies. In some embodiments, the methods disclosed herein can be used to reduce the tumor size of a tumor derived from, for example, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T cell lymphoma, environmentally induced cancers including those induced by asbestos, other B cell malignancies, and combinations of said cancers. In some embodiments, the cancer is multiple myeloma. The particular cancer can be responsive to chemo- or radiation therapy or the cancer can be refractory. A refractor cancer refers to a cancer that is not amendable to surgical intervention and the cancer is either initially unresponsive to chemo- or radiation therapy or the cancer becomes unresponsive over time.

An "anti-tumor effect" as used herein, refers to a biological effect that can present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect can also refer to the prevention of the occurrence of a tumor, e.g., a vaccine.

A "cytokine," as used herein, refers to a non-antibody protein that is released by one cell in response to contact with a specific antigen, wherein the cytokine interacts with a second cell to mediate a response in the second cell. "Cytokine" as used herein is meant to refer to proteins released by one cell population that act on another cell as intercellular mediators. A cytokine can be endogenously expressed by a cell or administered to a subject. Cytokines may be released by immune cells, including macrophages, B cells, T cells, and mast cells to propagate an immune response. Cytokines can induce various responses in the recipient cell. Cytokines can include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines can promote an inflammatory response. Examples of homeostatic cytokines include, but are not limited to, IL-2, IL-4, IL-5, IL-7, IL-10, IL-12p40, IL-12p70, IL-15, and interferon (IFN) gamma. Examples of pro-inflammatory cytokines include, but are not limited to, IL-1a, IL-1b, IL-6, IL-13, IL-17a, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), and perforin. Examples of acute phase-proteins include, but are not limited to, C-reactive protein (CRP) and serum amyloid A (SAA).

"Chemokines" are a type of cytokine that mediates cell chemotaxis, or directional movement. Examples of chemokines include, but are not limited to, IL-8, IL-16, eotaxin, eotaxin-3, macrophage-derived chemokine (MDC or CCL22), monocyte chemotactic protein 1 (MCP-1 or CCL2), MCP-4, macrophage inflammatory protein 1α (MIP-1α, MIP-1a), MIP-1β (MIP-1b), gamma-induced protein 10 (IP-10), and thymus and activation regulated chemokine (TARC or CCL17).

As used herein, "chimeric receptor" refers to an engineered surface expressed molecule capable of recognizing a particular molecule. Chimeric antigen receptors (CARs) and engineered T cell receptors (TCRs), which comprise binding domains capable of interacting with a particular tumor antigen, allow T cells to target and kill cancer cells that express the particular tumor antigen.

A "therapeutically effective amount," "effective dose," "effective amount," or "therapeutically effective dosage" of a therapeutic agent, e.g., engineered CAR T cells, is any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

The term "lymphocyte" as used herein includes natural killer (NK) cells, T cells, or B cells. NK cells are a type of cytotoxic (cell toxic) lymphocyte that represent a major component of the inherent immune system. NK cells reject tumors and cells infected by viruses. It works through the process of apoptosis or programmed cell death. They were termed "natural killers" because they do not require activation in order to kill cells. T cells play a major role in cell-mediated-immunity (no antibody involvement). Its T cell receptors (TCR) differentiate themselves from other lymphocyte types. The thymus, a specialized organ of the immune system, is primarily responsible for the T cell's maturation. There are six types of T cells, namely: Helper T cells (e.g., CD4+ cells), Cytotoxic T cells (also known as TC, cytotoxic T lymphocyte, CTL, T-killer cell, cytolytic T cell, CD8+ T cells or killer T cell), Memory T cells ((i) stem memory TSCM cells, like naive cells, are CD45RO−, CCR7+, CD45RA+, CD62L+(L-selectin), CD27+, CD28+ and IL-7Rα+, but they also express large amounts of CD95, IL-2Rβ, CXCR3, and LFA-1, and show numerous functional attributes distinctive of memory cells); (ii) central memory TCM cells express L-selectin and the CCR7, they secrete IL-2, but not IFNγ or IL-4, and (iii) effector memory TEM cells, however, do not express L-selectin or CCR7 but produce effector cytokines like IFNγ and IL-4), Regulatory T cells (Tregs, suppressor T cells, or CD4+CD25+ regulatory T cells), Natural Killer T cells (NKT) and Gamma Delta T cells. B-cells, on the other hand, play a principal role in humoral immunity (with antibody involvement). It makes antibodies and antigens and performs the role of antigen-presenting cells (APCs) and turns into memory B-cells after activation by antigen interaction. In mammals, immature B-cells are formed in the bone marrow, where its name is derived from.

The term "genetically engineered" or "engineered" refers to a method of modifying the genome of a cell, including, but not limited to, deleting a coding or non-coding region or a portion thereof or inserting a coding region or a portion thereof. In some embodiments, the cell that is modified is a lymphocyte, e.g., a T cell, which can either be obtained from a patient or a donor. The cell can be modified to express an exogenous construct, such as, e.g., a chimeric antigen receptor (CAR) or a T cell receptor (TCR), which is incorporated into the cell's genome.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy include, but are not limited to, T cell therapies. T cell therapy can include adoptive T cell therapy, tumor-infiltrating lymphocyte (TIL) immunotherapy, autologous cell therapy, engineered autologous cell therapy (eACT™), and allogeneic T cell transplantation. However, one of skill in the art would recognize that the conditioning methods disclosed herein would enhance the effectiveness of any transplanted T cell therapy. Examples of T cell therapies are described in U.S. Patent Publication Nos. 2014/0154228 and 2002/0006409, U.S. Pat. Nos. 7,741,465, 6,319,494, 5,728,388, and International Patent Application Publication No. WO 2008/081035.

The T cells of the immunotherapy can come from any source known in the art. For example, T cells can be differentiated in vitro from a hematopoietic stem cell population, or T cells can be obtained from a subject. T cells can be obtained from, e.g., peripheral blood mononuclear cells (PBMCs), bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by references in its entirety.

The term "engineered Autologous Cell Therapy," which can be abbreviated as "eACT™," also known as adoptive cell transfer, is a process by which a patient's own T cells are collected and subsequently genetically altered to recognize and target one or more antigens expressed on the cell surface of one or more specific tumor cells or malignancies. T cells can be engineered to express, for example, chimeric antigen receptors (CAR). CAR positive (+) T cells are engineered to express an extracellular single chain variable fragment (scFv) with specificity for a particular tumor antigen linked to an intracellular signaling part comprising at least one costimulatory domain and at least one activating domain. The CAR scFv can be designed to target, for example, CD19, which is a transmembrane protein expressed by cells in the B cell lineage, including all normal B cells and B cell malignances, including but not limited to diffuse large B-cell lymphoma (DLBCL) not otherwise specified, primary mediastinal large B-cell lymphoma, high grade B-cell lymphoma, and DLBCL arising from follicular lymphoma, NHL, CLL, and non-T cell ALL. Example CART cell therapies and constructs are described in U.S. Patent Publication Nos. 2013/0287748, 2014/0227237, 2014/0099309, and 2014/0050708, and these references are incorporated by reference in their entirety.

A "patient" as used herein includes any human who is afflicted with a cancer (e.g., a lymphoma or a leukemia). The terms "subject" and "patient" are used interchangeably herein.

As used herein, the term "in vitro cell" refers to any cell which is cultured ex vivo. In particular, an in vitro cell can include a T cell.

The terms "peptide," "polypeptide," and "protein" are used interchangeably, and refer to a compound comprised of amino acid residues covalently linked by peptide bonds. A protein or peptide contains at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

"Stimulation," as used herein, refers to a primary response induced by binding of a stimulatory molecule with its cognate ligand, wherein the binding mediates a signal transduction event. A "stimulatory molecule" is a molecule on a T cell, e.g., the T cell receptor (TCR)/CD3 complex that specifically binds with a cognate stimulatory ligand present on an antigen present cell. A "stimulatory ligand" is a ligand that when present on an antigen presenting cell (e.g., an APC, a dendritic cell, a B-cell, and the like) can specifically bind with a stimulatory molecule on a T cell, thereby mediating a primary response by the T cell, including, but not limited to, activation, initiation of an immune response, proliferation, and the like. Stimulatory ligands include, but are not limited to, an anti-CD3 antibody, an MHC Class I molecule loaded with a peptide, a superagonist anti-CD2 antibody, and a superagonist anti-CD28 antibody.

A "costimulatory signal," as used herein, refers to a signal, which in combination with a primary signal, such as TCR/CD3 ligation, leads to a T cell response, such as, but not limited to, proliferation and/or upregulation or down regulation of key molecules.

A "costimulatory ligand," as used herein, includes a molecule on an antigen presenting cell that specifically binds a cognate co-stimulatory molecule on a T cell. Binding of the costimulatory ligand provides a signal that mediates a T cell response, including, but not limited to, proliferation, activation, differentiation, and the like. A costimulatory ligand induces a signal that is in addition to the primary signal provided by a stimulatory molecule, for instance, by binding of a T cell receptor (TCR)/CD3 complex with a major histocompatibility complex (MHC) molecule loaded with peptide. A co-stimulatory ligand can include, but is not limited to, 3/TR6, 4-1BB ligand, agonist or antibody that binds Toll ligand receptor, B7-1 (CD80), B7-2 (CD86), CD30 ligand, CD40, CD7, CD70, CD83, herpes virus entry mediator (HVEM), human leukocyte antigen G (HLA-G), ILT4, immunoglobulin-like transcript (ILT) 3, inducible costimulatory ligand (ICOS-L), intercellular adhesion molecule (ICAM), ligand that specifically binds with B7-H3, lymphotoxin beta receptor, MHC class I chain-related protein A (MICA), MEW class I chain-related protein B (MICB), OX40 ligand, PD-L2, or programmed death (PD) L1. A co-stimulatory ligand includes, without limitation, an antibody that specifically binds with a co-stimulatory molecule present on a T cell, such as, but not limited to, 4-1BB, B7-H3, CD2, CD27, CD28, CD30, CD40, CD7, ICOS, ligand that specifically binds with CD83, lymphocyte function-associated antigen-1 (LFA-1), natural killer cell receptor C (NKG2C), OX40, PD-1, or tumor necrosis factor superfamily member 14 (TNFSF14 or LIGHT).

A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, 4-1BB/CD137, B7-H3, BAFFR, BLAME (SLAMF8), BTLA, CD 33, CD 45, CD100 (SEMA4D), CD103, CD134, CD137, CD154, CD16, CD160 (BY55), CD18, CD19, CD19a, CD2, CD22, CD247, CD27, CD276 (B7-H3), CD28, CD29, CD3 (alpha; beta; delta; epsilon; gamma; zeta), CD30, CD37, CD4, CD4, CD40, CD49a, CD49D, CD49f, CD5, CD64, CD69, CD7, CD80, CD83 ligand, CD84, CD86, CD8alpha, CD8beta, CD9, CD96 (Tactile), CD1-1a, CD1-1b, CD1-1c, CD1-1d, CDS, CEACAM1, CRT AM, DAP-10, DNAM1 (CD226), Fc gamma receptor, GADS, GITR, HVEM (LIGHTR), IA4, ICAM-1, ICAM-1, ICOS, Ig alpha (CD79a), IL2R beta, IL2R gamma, IL7R alpha, integrin, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, LIGHT, LIGHT (tumor necrosis factor superfamily member 14; TNFSF14), LTBR, Ly9 (CD229), lymphocyte function-associated antigen-1 (LFA-1 (CD11a/CD18), MHC class I molecule, NKG2C, NKG2D, NKp30, NKp44, NKp46, NKp80 (KLRF1), OX40, PAG/Cbp, PD-1, PSGL1, SELPLG (CD162), signaling lymphocytic activation molecule, SLAM (SLAMF1; CD150; IPO-3), SLAMF4 (CD244; 2B4), SLAMF6 (NTB-A; Ly108), SLAMF7, SLP-76, TNF, TNFr, TNFR2, Toll ligand receptor, TRANCE/RANKL, VLA1, or VLA-6, or fragments, truncations, or combinations thereof.

The terms "reducing" and "decreasing" are used interchangeably herein and indicate any change that is less than the original. "Reducing" and "decreasing" are relative terms, requiring a comparison between pre- and post-measurements. "Reducing" and "decreasing" include complete depletions.

"Treatment" or "treating" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease. In some embodiments, "treatment" or "treating" includes a partial remission. In another embodiment, "treatment" or "treating" includes a complete remission.

Various aspects of the disclosure are described in further detail in the following subsections.

Characterization of the Tumor Microenvironment (TME)

The present disclosure provides methods to characterize the TME using gene expression profiling and/or intratumoral T cell density measurement prior to treatment with a chimeric receptor therapy (e.g., axicabtagene ciloleucel (axi-cel)). As described herein, the TME characteristics utilizing pre-specified gene sets (e.g., Immunosign®21, Pan Cancer) and immune scores (e.g., Immunosign®21) and/or intratumoral T cell density measurements or indices (e.g., Immunoscore®) associate with clinical outcomes of chimeric receptor therapy (e.g., axicabtagene ciloleucel (axi-cel)).

Patient biopsies can be used as starting material to analyze the tumor microenvironment using gene expression profiling (e.g., digital gene expression using NanoString™). In some embodiments, the patient biopsy is obtained prior to treatment with a chimeric receptor therapy (e.g., axicabtagene ciloleucel (axi-cel)).

A bioinformatics method can be used to generate an immune score or scores to characterize the TME. In some embodiments, the immune score is a measure of immune related genes that provides information regarding adaptive immunity including T cell cytotoxicity, T cell differentiation, T cell attraction, T cell adhesion and immune suppression including immune orientation, angiogenesis suppression, immune co-inhibition, and cancer stem cells. The bioinformatics method can also include T cell-specific (effector T cell, Th1) genes, interferon pathway-related genes, chemokines, and immune checkpoints.

An expression profiling assay (e.g., The Immunosign® Clinical Research assay utilizes the nCounter® technology (NanoString)) can be used to measure the gene expression level of multiple immune genes in a multiplex format. In some embodiments, a high/low immune score (e.g., Immunosign®21 score) cut-off can be defined as the 25th percentile of the observed scores among samples. In some embodiments, the high score indicates expression of immune-related genes potentially associated with tumor response.

In some embodiments, the immune score is a measure of intratumoral T cell density. Intratumoral T cell density can be determined by, for example, detecting and quantifying T cells, such as CD3+ T cells and/or CD8+ T cells, in the tumor microenvironment. For example, tumor biopsies can be sectioned and stained or labeled for T cell markers such as CD3 and/or CD8, and the relative or absolute abundance of T cells can be quantified by a pathologist or determined using dedicated digital pathology software. In some embodiments, a high/low immune score (e.g., Immunoscore®) is assigned based on intratumoral T cell density. A high/low immune score threshold can be defined, for example, as the median score observed among samples. In some embodiments, intratumoral T cell density is determined using flow cytometry and/or protein-based assays such as western blotting and ELISA.

Expression and tumor-infiltrating T lymphocyte analysis and scoring can be used to examine associations between TME features and response. In some embodiments, objective response (OR) is determined per the revised IWG Response Criteria for Malignant Lymphoma (Cheson, 2007) and determined by IWG Response Criteria for Malignant Lymphoma (Cheson et al. *Journal of Clinical Oncology* 32, no. 27 (September 2014) 3059-3067). In some embodiments, Duration of Response is assessed. In some embodiments, Progression-Free Survival (PFS) by investigator assessment per Lugano Response Classification Criteria is evaluated.

Chimeric Antigen Receptors and T Cell Receptors

Chimeric antigen receptors (CARs or CAR-Ts) are genetically engineered receptors. These engineered receptors can be readily inserted into and expressed by immune cells, including T cells in accordance with techniques known in the art. With a CAR, a single receptor can be programmed to both recognize a specific antigen and, when bound to that antigen, activate the immune cell to attack and destroy the cell bearing that antigen. When these antigens exist on tumor cells, an immune cell that expresses the CAR can target and kill the tumor cell. Chimeric antigen receptors incorporate costimulatory (signaling) domains to increase their potency. See U.S. Pat. Nos. 7,741,465, and 6,319,494, as well as Krause et al. and Finney et al. (supra), Song et al., Blood 119:696-706 (2012); Kalos et al., Sci. Transl. Med. 3:95 (2011); Porter et al., N. Engl. J. Med. 365:725-33 (2011), and Gross et al., Annu. Rev. Pharmacol. Toxicol. 56:59-83 (2016).

In some embodiments, a costimulatory domain which includes a truncated hinge domain ("THD") further comprises some or all of a member of the immunoglobulin family such as IgG1, IgG2, IgG3, IgG4, IgA, IgD, IgE, IgM, or fragment thereof.

In some embodiments, the THD is derived from a human complete hinge domain ("CHD"). In other embodiments, the THD is derived from a rodent, murine, or primate (e.g., non-human primate) CHD of a costimulatory protein. In some embodiments, the THD is derived from a chimeric CHD of a costimulatory protein.

The costimulatory domain for the CAR or TCR of the invention can further comprise a transmembrane domain and/or an intracellular signaling domain. The transmembrane domain can be designed to be fused to the extracellular domain of the CAR. It can similarly be fused to the intracellular domain of the CAR. In some embodiments, the transmembrane domain that naturally is associated with one of the domains in a CAR is used. In some instances, the transmembrane domain can be selected or modified by amino acid substitution to avoid binding of such domains to the transmembrane domains of the same or different surface membrane proteins to minimize interactions with other members of the receptor complex. The transmembrane domain can be derived either from a natural or from a synthetic source. Where the source is natural, the domain can be derived from any membrane-bound or transmembrane protein. Transmembrane regions of particular use in this invention can be derived from (i.e., comprise) 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD3 zeta, CD30, CD4, CD40, CD49a, CD49D, CD49f, CD69, CD7, CD84, CD8, CD8alpha, CD8beta, CD96 (Tactile), CD11a, CD11b, CD11c, CD11d, CDS, CEACAM1, CRT AM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, a ligand that specifically binds with CD83, LIGHT, LTBR, Ly9 (CD229), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A; Ly108), SLAMF7, SLP-76, TNF receptor proteins, TNFR2, TNFSF14, a Toll ligand receptor, TRANCE/RANKL, VLA1, or VLA-6, or a fragment, truncation, or a combination thereof.

Optionally, short linkers can form linkages between any or some of the extracellular, transmembrane, and intracellular domains of the CAR. In some embodiments, the linker may be derived from repeats of glycine-glycine-glycine-glycine-serine (G4S)n (SEQ ID NO: 2) or GST-SGSGKPGSGEGSTKG (SEQ ID NO: 1). In some embodiments, the linker comprises 3-20 amino acids and an amino acid sequence at least 80%, 81%, 82%, 83%, 84%, 85%, 86%, 87%, 88%, 89%, 90%, 91%, 92%, 93%, 94%, 95%, 96%, 97%, 98%, 99% or 100% identical to GST-SGSGKPGSGEGSTKG (SEQ ID NO: 1).

The linkers described herein, may also be used as a peptide tag. The linker peptide sequence can be of any appropriate length to connect one or more proteins of interest and is preferably designed to be sufficiently flexible so as to allow the proper folding and/or function and/or activity of one or both of the peptides it connects. Thus, the linker peptide can have a length of no more than 10, no more than 11, no more than 12, no more than 13, no more than 14, no more than 15, no more than 16, no more than 17, no more than 18, no more than 19, or no more than 20 amino acids. In some embodiments, the linker peptide can have a length of at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 amino acids. In some embodiments, the linker comprises at least 7 and no more than 20 amino acids, at least 7 and no more than 19 amino acids, at least 7 and no more than 18 amino acids, at least 7 and no more than 17 amino acids, at least 7 and no more than 16 amino acids, at least 7 and no more 15 amino acids, at least 7 and no more than 14 amino acids, at least 7 and no more than 13 amino acids, at least 7 and no more than 12 amino acids or at least 7 and no more than 11 amino acids. In certain embodiments, the linker comprises 15-17 amino acids, and in particular embodiments, comprises 16 amino acids. In some embodiments, the linker comprises 10-20 amino acids. In some embodiments, the linker comprises 14-19 amino acids. In some embodiments, the linker comprises 15-17 amino acids. In some embodiments, the linker comprises 15-16 amino acids. In some embodiments, the linker comprises 16 amino acids. In some embodiments, the linker comprises 3, 4, 5, 6, 7, 8, 9, 10, 11, 12, 13, 14, 15, 16, 17, 18, 19 or 20 amino acids.

In some embodiments, a spacer domain is used. In some embodiments, the spacer domain is derived from CD4, CD8a, CD8b, CD28, CD28T, 4-1BB, or other molecule described herein. In some embodiments, the spacer domains may include a chemically induced dimerizer to control expression upon addition of a small molecule. In some embodiments, a spacer is not used.

The intracellular (signaling) domain of the engineered T cells of the invention can provide signaling to an activating domain, which then activates at least one of the normal effector functions of the immune cell. Effector function of a T cell, for example, can be cytolytic activity or helper activity including the secretion of cytokines.

In certain embodiments, suitable intracellular signaling domain include (i.e., comprise), but are not limited to 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8, CD8alpha, CD8beta, CD96 (Tactile), CD11a, CD11b, CD11c, CD11d, CDS, CEACAM1, CRT AM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, ligand that specifically binds with CD83, LIGHT, LTBR, Ly9 (CD229), Ly108), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A, SLAMF7, SLP-76, TNF receptor proteins, TNFR2, TNFSF14, a Toll ligand receptor, TRANCE/RANKL, VLA1, or VLA-6, or a fragment, truncation, or a combination thereof.

In some embodiments, the chimeric antigen receptor (CAR) is axicabtagene ciloleucel (axi-cel). Axicabtagene ciloleucel (axi-cel) is an autologous anti-CD19 chimeric antigen receptor (CAR) T cell therapy (FIG. 1). Axicabtagene ciloleucel (axi-cel) (YESCARTA™) is approved by the US Food and Drug Administration for the treatment of patients with relapsed or refractory large B cell lymphoma with ≥2 prior systemic therapies. (Yescarta (axicabtagene ciloleucel) [package insert]. Santa Monica, CA: Kite Pharma; 2017).

A TCR may be introduced to convey antigen reactivity. In some embodiments, the antigen reactivity is restricted by MHC presentation of a peptide. The TCR may be an alpha/beta TCR, gamma/delta TCR, or other. In some embodiments, the TCR is an HPV-16 E7 TCR with murine constant chains (2A linked). In some embodiments, the chains may be linked by an IRES or any 2A family members' sequence (e.g., P2A, T2A, E2A, F2A, etc). In some embodiments, the TCR is an HPV recognizing TCR, or other viral reactive TCR (e.g., EBV, influenza, etc.). In some embodiments, a cancer or cancer associated antigen reactive TCR may be used (e.g., NYESO, MART1, gp100, etc.)

In some embodiments, the TCR is a TCR of normal/healthy peptide reactivity or other antigen reactivity/restriction. In some embodiments, the TCR is reactive against murine or other non-human MHC. In some embodiments, the TCR is a class I or class II restricted TCR.

Antigen Binding Molecules

Suitable CARs can be engineered to bind to an antigen (such as a cell-surface antigen) by incorporating an antigen binding molecule that interacts with that targeted antigen. In some embodiments, the antigen binding molecule is an antibody fragment thereof, e.g., one or more single chain antibody fragment ("scFv"). A scFv is a single chain antibody fragment having the variable regions of the heavy and light chains of an antibody linked together. See U.S. Pat. Nos. 7,741,465 and 6,319,494, as well as Eshhar et al., Cancer Immunol Immunotherapy (1997) 45: 131-136. A scFv retains the parent antibody's ability to interact specifically with target antigen. scFv's are useful in chimeric antigen receptors because they can be engineered to be expressed as part of a single chain along with the other CAR components. Id. See also Krause et al., J. Exp. Med., Volume 188, No. 4, 1998 (619-626); Finney et al., *Journal of Immunology*, 1998, 161: 2791-2797. It will be appreciated that the antigen binding molecule is typically contained within the extracellular portion of the CAR such that it is capable of recognizing and binding to the antigen of interest. Bispecific and multispecific CARs are contemplated within the scope of the invention, with specificity to more than one target of interest.

In some embodiments, the polynucleotide encodes a CAR or a TCR comprising a THD of the present invention and an antigen binding molecule that specifically binds to a target antigen. In some embodiments, the target antigen is a tumor antigen. In some embodiments, the antigen is selected from a tumor-associated surface antigen, such as 5T4, alphafetoprotein (AFP), B7-1 (CD80), B7-2 (CD86), BCMA, B-human chorionic gonadotropin, CA-125, carcinoembryonic antigen (CEA), carcinoembryonic antigen (CEA), CD123, CD133, CD138, CD19, CD20, CD22, CD23, CD24, CD25, CD30, CD33, CD34, CD4, CD40, CD44, CD56, CD8, CLL-1, c-Met, CMV-specific antigen, CS-1, CSPG4, CTLA-4, DLL3, disialoganglioside GD2, ductal-epithelial mucine, EBV-specific antigen, EGFR variant III (EGFRvIII), ELF2M, endoglin, ephrin B2, epidermal growth factor receptor (EGFR), epithelial cell adhesion molecule (EpCAM), epithelial tumor antigen, ErbB2 (HER2/neu), fibroblast associated protein (fap), FLT3, folate binding protein, GD2, GD3, glioma-associated antigen, glycosphingolipids, gp36, HBV-specific antigen, HCV-specific antigen, HER1-HER2, HER2-HER3 in combination, HERV-K, high molecular weight-melanoma associated antigen (HMW-MAA), HIV-1 envelope glycoprotein gp41, HPV-specific antigen, human telomerase reverse transcriptase, IGFI receptor, IGF-II, IL-11Ralpha, IL-13R-a2, Influenza Virus-specific antigen; CD38, insulin growth factor (IGFI)-1, intestinal carboxyl esterase, kappa chain, LAGA-1a, lambda chain, Lassa Virus-specific antigen, lectin-reactive AFP, lineage-specific or tissue specific antigen such as CD3, MAGE, MAGE-A1, major histocompatibility complex (MHC) molecule, major histocompatibility complex (MHC) molecule presenting a tumor-specific peptide epitope, M-CSF, melanoma-associated antigen, mesothelin, MN-CA IX, MUC-1, mut hsp70-2, mutated p53, mutated p53, mutated ras, neutrophil elastase, NKG2D, Nkp30, NY-ESO-1, p53, PAP, prostase, prostate specific antigen (PSA), prostate-carcinoma tumor antigen-1 (PCTA-1), prostate-specific antigen protein, STEAP1, STEAP2, PSMA, RAGE-1, ROR1, RU1, RU2 (AS), surface adhesion molecule, surviving and telomerase, TAG-72, the extra domain A (EDA) and extra domain B (EDB) of fibronectin and the A1 domain of tenascin-C (TnC A1), thyroglobulin, tumor stromal antigens, vascular endothelial growth factor receptor-2 (VEGFR2), virus-specific surface antigen such as an HIV-specific antigen (such as HIV gp120), as well as any derivate or variant of these surface markers.

Engineered T Cells and Uses

The cell of the present disclosure may be obtained through T cells obtained from a subject. T cells can be obtained from, e.g., peripheral blood mononuclear cells, bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. In some embodiments, the cells collected by apheresis are washed to remove the plasma fraction, and placed in an appropriate buffer or media for subsequent processing. In some embodiments, the cells are washed with PBS. As will be appreciated, a washing step can be used, such as by using a semiautomated flow through centrifuge, e.g., the Cobe™ 2991 cell processor, the Baxter CytoMate™, or the like. In some embodiments, the washed cells are resuspended in one or more biocompatible buffers, or other saline solution with or without buffer. In some embodiments, the undesired components of the apheresis sample are removed. Additional methods of isolating T cells for a T cell therapy are disclosed in U.S. Patent Pub. No. 2013/0287748, which is herein incorporated by references in its entirety.

In some embodiments, T cells are isolated from PBMCs by lysing the red blood cells and depleting the monocytes, e.g., by using centrifugation through a PERCOLL™ gradient. In some embodiments, a specific subpopulation of T cells, such as CD4+, CD8+, CD28+, CD45RA+, and CD45RO+ T cells is further isolated by positive or negative selection techniques known in the art. For example, enrichment of a T cell population by negative selection can be accomplished with a combination of antibodies directed to surface markers unique to the negatively selected cells. In some embodiments, cell sorting and/or selection via negative magnetic immunoadherence or flow cytometry that uses a cocktail of monoclonal antibodies directed to cell surface markers present on the cells negatively selected can be used. For example, to enrich for CD4+ cells by negative selection, a monoclonal antibody cocktail typically includes antibodies to CD8, CD11b, CD14, CD16, CD20, and HLA-DR. In some embodiments, flow cytometry and cell sorting are used to isolate cell populations of interest for use in the present disclosure.

In some embodiments, PBMCs are used directly for genetic modification with the immune cells (such as CARs) using methods as described herein. In some embodiments, after isolating the PBMCs, T lymphocytes are further isolated, and both cytotoxic and helper T lymphocytes are sorted into naive, memory, and effector T cell subpopulations either before or after genetic modification and/or expansion.

In some embodiments, CD8+ cells are further sorted into naive, central memory, and effector cells by identifying cell surface antigens that are associated with each of these types of CD8+ cells. In some embodiments, the expression of phenotypic markers of central memory T cells includes expression of CCR7, CD3, CD28, CD45RO, CD62L, and CD127 and negative for granzyme B. In some embodiments, central memory T cells are CD8+, CD45RO+, and CD62L+ T cells. In some embodiments, effector T cells are negative for CCR7, CD28, CD62L, and CD127 and positive for granzyme B and perforin. In some embodiments, CD4+ T cells are further sorted into subpopulations. For example, CD4+ T helper cells can be sorted into naive, central memory, and effector cells by identifying cell populations that have cell surface antigens.

In some embodiments, the immune cells, e.g., T cells, are genetically modified following isolation using known methods, or the immune cells are activated and expanded (or differentiated in the case of progenitors) in vitro prior to being genetically modified. In another embodiment, the immune cells, e.g., T cells, are genetically modified with the chimeric antigen receptors described herein (e.g., transduced with a viral vector comprising one or more nucleotide sequences encoding a CAR or TCR) and then are activated and/or expanded in vitro. Methods for activating and expanding T cells are known in the art and are described, e.g., in U.S. Pat. Nos. 6,905,874; 6,867,041; and 6,797,514; and International Patent Application Publication No. WO 2012/079000, the contents of which are hereby incorporated by reference in their entirety. Generally, such methods include contacting PBMC or isolated T cells with a stimulatory agent and costimulatory agent, such as anti-CD3 and anti-CD28 antibodies, generally attached to a bead or other surface, in a culture medium with appropriate cytokines, such as IL-2. Anti-CD3 and anti-CD28 antibodies attached to the same bead serve as a "surrogate" antigen presenting cell (APC). One example is the Dynabeads® system, a CD3/CD28 activator/stimulator system for physiological activation of human T cells. In other embodiments, the T cells are activated and stimulated to proliferate with feeder cells and appropriate antibodies and cytokines using methods such as those described in U.S. Pat. Nos. 6,040,177 and 5,827,642 and International Patent Application Publication No. WO 2012/129514, the contents of which are hereby incorporated by reference in their entirety.

In some embodiments, the T cells are obtained from a donor subject. In some embodiments, the donor subject is human patient afflicted with a cancer or a tumor. In some embodiments, the donor subject is a human patient not afflicted with a cancer or a tumor.

In some embodiments, the composition comprises a pharmaceutically acceptable carrier, diluent, solubilizer, emulsifier, preservative and/or adjuvant. In some embodiments, the composition comprises an excipient.

In some embodiments, the composition is selected for parenteral delivery, for inhalation, or for delivery through the digestive tract, such as orally. The preparation of such pharmaceutically acceptable compositions is within the ability of one skilled in the art. In some embodiments, buffers are used to maintain the composition at physiological pH or at a slightly lower pH, typically within a pH range of from about 5 to about 8. In some embodiments, when parenteral administration is contemplated, the composition is in the form of a pyrogen-free, parenterally acceptable aqueous solution comprising a composition described herein, with or without additional therapeutic agents, in a pharmaceutically acceptable vehicle. In some embodiments, the vehicle for parenteral injection is sterile distilled water in which composition described herein, with or without at least one additional therapeutic agent, is formulated as a sterile, isotonic solution, properly preserved. In some embodiments, the preparation involves the formulation of the desired molecule with polymeric compounds (such as polylactic acid or polyglycolic acid), beads or liposomes, that provide for the controlled or sustained release of the product, which are then be delivered via a depot injection. In some embodiments, implantable drug delivery devices are used to introduce the desired molecule.

In some embodiments, the methods of treating a cancer in a subject in need thereof comprise a T cell therapy. In some embodiments, the T cell therapy disclosed herein is engineered Autologous Cell Therapy (eACT™). According to this embodiment, the method can include collecting blood cells from the patient. The isolated blood cells (e.g., T cells) can then be engineered to express a CAR or a TCR disclosed herein. In a particular embodiment, the CAR T cells or the TCR T cells are administered to the patient. In some embodiments, the CAR T cells or the TCR T cells treat a tumor or a cancer in the patient. In some embodiments the CAR T cells or the TCR T cells reduce the size of a tumor or a cancer.

In some embodiments, the donor T cells for use in the T cell therapy are obtained from the patient (e.g., for an autologous T cell therapy). In other embodiments, the donor T cells for use in the T cell therapy are obtained from a subject that is not the patient.

In some embodiments, the T cells can be administered at a therapeutically effective amount. For example, a therapeutically effective amount of the T cells can be at least about $10^4$ cells, at least about $10^5$ cells, at least about $10^6$ cells, at least about $10^7$ cells, at least about $10^8$ cells, at least about $10^9$, or at least about $10^{10}$. In another embodiment, the therapeutically effective amount of the T cells is about $10^4$ cells, about $10^5$ cells, about $10^6$ cells, about $10^7$ cells, or about $10^8$ cells. In some embodiments, the therapeutically effective amount of the CAR T cells is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg.

In some embodiments, the therapeutically effective amount of the CAR-positive viable T cells is between about $1\times10^6$ and about $2\times10^6$ CAR-positive viable T cells per kg body weight up to a maximum dose of about $1\times10^8$ CAR-positive viable T cell.

Methods of Treatment

The methods disclosed herein can be used to treat a cancer in a subject, reduce the size of a tumor, kill tumor cells, prevent tumor cell proliferation, prevent growth of a tumor, eliminate a tumor from a patient, prevent relapse of a tumor, prevent tumor metastasis, induce remission in a patient, or any combination thereof. In some embodiments, the methods induce a complete response. In other embodiments, the methods induce a partial response.

In some embodiments, the present disclosure provides a predictive tool for clinical efficacy of T cell therapy, by analyzing tumor microenvironment prior to treatment.

Methods of the present invention can also be used in companion testing to inform on whether additional therapies, in combination or used sequentially, will be more effective in subjects with certain tumor microenvironment characteristics. In some embodiments, additional treatments can be cytokines (e.g., IL-2, IL-15), stimulating antibodies (e.g., anti-41BB, OX-40), checkpoint blockade (e.g., CTLA4, PD-1), or innate immune stimulators (e.g., TLR, STING agonists). In some embodiments, additional treatments can be T cell-recruiting chemokines (e.g., CCL2, CCL1, CCL22, CCL17, and combinations thereof) and/or T cells. In some embodiments, the additional therapy or therapies are administered systemically or intratumorally.

Cancers that may be treated include tumors that are not vascularized, not yet substantially vascularized, or vascularized. The cancer may also include solid or non-solid tumors. In some embodiments, the cancer is a hematologic cancer. In some embodiments, the cancer is of the white blood cells. In other embodiments, the cancer is of the plasma cells. In some embodiments, the cancer is leukemia, lymphoma, or myeloma. In some embodiments, the cancer is acute lymphoblastic leukemia (ALL) (including non T cell ALL), acute lymphoid leukemia (ALL), and hemophagocytic lymphohistocytosis (HLH)), B cell prolymphocytic leukemia, B-cell acute lymphoid leukemia ("BALL"), blastic plasmacytoid dendritic cell neoplasm, Burkitt's lymphoma, chronic lymphocytic leukemia (CLL), chronic myelogenous leukemia (CML), chronic myeloid leukemia (CML), chronic or acute granulomatous disease, chronic or acute leukemia, diffuse large B cell lymphoma, diffuse large B cell lymphoma (DLBCL), follicular lymphoma, follicular lymphoma (FL), hairy cell leukemia, hemophagocytic syndrome (Macrophage Activating Syndrome (MAS), Hodgkin's Disease, large cell granuloma, leukocyte adhesion deficiency, malignant lymphoproliferative conditions, MALT lymphoma, mantle cell lymphoma, Marginal zone lymphoma, monoclonal gammapathy of undetermined significance (MGUS), multiple myeloma, myelodysplasia and myelodysplastic syndrome (MDS), myeloid diseases including but not limited to acute myeloid leukemia (AML), non-Hodgkin's lymphoma (NHL), plasma cell proliferative disorders (e.g., asymptomatic myeloma (smoldering multiple myeloma or indolent myeloma), plasmablastic lymphoma, plasmacytoid dendritic cell neoplasm, plasmacytomas (e.g., plasma cell dyscrasia; solitary myeloma; solitary plasmacytoma; extramedullary plasmacytoma; and multiple plasmacytoma), POEMS syndrome (Crow-Fukase syndrome; Takatsuki disease; PEP syndrome), primary mediastinal large B cell lymphoma (PMBC), small cell- or a large cell-follicular lymphoma, splenic marginal zone lymphoma (SMZL), systemic amyloid light chain amyloidosis, T cell acute lymphoid leukemia ("TALL"), T cell lymphoma, transformed follicular lymphoma, Waldenstrom macroglobulinemia, or a combination thereof.

In some embodiments, the cancer is a myeloma. In some embodiments, the cancer is multiple myeloma. In some embodiments, the cancer is leukemia. In some embodiments, the cancer is acute myeloid leukemia.

In some embodiments, the methods further comprise administering a chemotherapeutic. In some embodiments, the chemotherapeutic selected is a lymphodepleting (preconditioning) chemotherapeutic. Beneficial preconditioning treatment regimens, along with correlative beneficial biomarkers are described in U.S. Provisional Patent Applications 62/262,143 and 62/167,750 which are hereby incorporated by reference in their entirety herein. These describe, e.g., methods of conditioning a patient in need of a T cell therapy comprising administering to the patient specified beneficial doses of cyclophosphamide (between 200 mg/m$^2$/day and 2000 mg/m$^2$/day) and specified doses of fludarabine (between 20 mg/m$^2$/day and 900 mg/m$^2$/day). One such dose regimen involves treating a patient comprising administering daily to the patient about 500 mg/m$^2$/day of cyclophosphamide and about 60 mg/m$^2$/day of fludarabine for three days prior to administration of a therapeutically effective amount of engineered T cells to the patient.

In some embodiments, the antigen binding molecule, transduced (or otherwise engineered) cells (such as CARs or TCRs), and the chemotherapeutic agent are administered each in an amount effective to treat the disease or condition in the subject.

In some embodiments, compositions comprising CAR-expressing immune effector cells disclosed herein may be administered in conjunction with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL', Bristol-Myers Squibb) and doxetaxel (TAXOTERE®, Rhone-Poulenc Rorer); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS2000; difluoromethylomithine (DMFO); retinoic acid derivatives such as Targretin™ (bexarotene), Panretin™, (alitretinoin); ONTAK™ (denileukin diftitox); esperamicins; capecitabine; and pharmaceutically acceptable salts, acids or derivatives of any of the above. In some embodiments, compositions comprising CAR- and/or TCR-expressing immune effector cells disclosed herein may be administered in conjunction with an anti-hormonal agent that acts to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. Combinations of chemotherapeutic agents are also administered where appropriate, including, but not limited to CHOP, i.e., Cyclophosphamide (Cytoxan®), Doxorubicin (hydroxydoxorubicin), Vincristine (Oncovin®), and Prednisone.

In some embodiments, the chemotherapeutic agent is administered at the same time or within one week after the administration of the engineered cell or nucleic acid. In other embodiments, the chemotherapeutic agent is administered from 1 to 4 weeks or from 1 week to 1 month, 1 week to 2 months, 1 week to 3 months, 1 week to 6 months, 1 week to 9 months, or 1 week to 12 months after the administration of the engineered cell or nucleic acid. In some embodiments, the chemotherapeutic agent is administered at least 1 month before administering the cell or nucleic acid. In some embodiments, the methods further comprise administering two or more chemotherapeutic agents.

A variety of additional therapeutic agents may be used in conjunction with the compositions described herein. For example, potentially useful additional therapeutic agents include PD-1 inhibitors such as nivolumab (OPDIVO®), pembrolizumab (KEYTRUDA®), pembrolizumab, pidilizumab (CureTech), and atezolizumab (Roche).

Additional therapeutic agents suitable for use in combination with the compositions and methods disclosed herein include, but are not limited to, ibrutinib (IMBRUVICA®), ofatumumab (ARZERRA®), rituximab (RITUXAN®), bevacizumab (AVASTIN®), trastuzumab (HERCEPTIN®), trastuzumab emtansine (KADCYLA®), imatinib (GLEEVEC®), cetuximab (ERBITUX®), panitumumab (VECTIBIX®), catumaxomab, ibritumomab, ofatumumab, tositumomab, brentuximab, alemtuzumab, gemtuzumab, erlotinib, gefitinib, vandetanib, afatinib, lapatinib, neratinib, axitinib, masitinib, pazopanib, sunitinib, sorafenib, toceranib, lestaurtinib, axitinib, cediranib, lenvatinib, nintedanib, pazopanib, regorafenib, semaxanib, sorafenib, sunitinib, tivozanib, toceranib, vandetanib, entrectinib, cabozantinib, imatinib, dasatinib, nilotinib, ponatinib, radotinib, bosutinib, lestaurtinib, ruxolitinib, pacritinib, cobimetinib, selumetinib, trametinib, binimetinib, alectinib, ceritinib, crizotinib, aflibercept, adipotide, denileukin diftitox, mTOR inhibitors such as Everolimus and Temsirolimus, hedgehog inhibitors such as sonidegib and vismodegib, CDK inhibitors such as CDK inhibitor (palbociclib).

In some embodiments, the composition comprising CAR immune cells are administered with an anti-inflammatory agent. Anti-inflammatory agents or drugs can include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), non-steroidal anti-inflammatory drugs (NSAIDS) including aspirin, ibuprofen, naproxen, methotrexate, sulfasalazine, leflunomide, anti-TNF medications, cyclophosphamide and mycophenolate. Exemplary NSAIDs include ibuprofen, naproxen, naproxen sodium, Cox-2 inhibitors, and sialylates. Exemplary analgesics include acetaminophen, oxycodone, tramadol of proporxyphene hydrochloride. Exemplary glucocorticoids include cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists, (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular), and minocycline.

In some embodiments, the compositions described herein are administered in conjunction with a cytokine. Examples of cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor (HGF); fibroblast growth factor (FGF); prolactin; placental lactogen; mullerian-inhibiting substance; mouse gonadotropin-associated peptide; inhibin; activin; vascular endothelial growth factor; integrin; thrombopoietin (TPO); nerve growth factors (NGFs) such as NGF-beta; platelet-growth factor; transforming growth factors (TGFs) such as TGF-alpha and TGF-beta; insulin-like growth factor-I and —II; erythropoietin (EPO, Epogen®, Procrit®); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

Administration

In some embodiments, engineered T cells described herein are used to treat a malignancy in a patient in methods comprising: (a) obtaining a plurality of T cells comprising one or more chimeric receptors; and (b) administering an effective dose of the T cells to the patient.

In some embodiments, the T cells can be administered at a therapeutically effective amount. For example, a therapeutically effective amount of the T cells can be at least about $10^4$ cells, at least about $10^5$ cells, at least about $10^6$ cells, at least about $10^7$ cells, at least about $10^8$ cells, at least about $10^9$ cells, or at least about $10^{10}$ cells. In another embodiment, the therapeutically effective amount of the T cells is about $10^4$ cells, about $10^5$ cells, about $10^6$ cells, about $10^7$ cells, or about $10^8$ cells. In some embodiments, the therapeutically effective amount of the CAR T cells is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg.

In some embodiments, the therapeutically effective amount of the CAR-positive viable T cells is between about $1\times10^6$ and about $2\times10^6$ CAR-positive viable T cells per kg body weight up to a maximum dose of about $1\times10^8$ CAR-positive viable T cell.

Monitoring

In some embodiments, administration of chimeric receptor T cell immunotherapy occurs at a certified healthcare facility.

In some embodiments, the methods disclosed herein comprise monitoring patients after administration of a chimeric receptor T cell immunotherapy (e.g., axicabtagene ciloleucel (axi-cel)) at least daily for 7 days at the certified healthcare facility following infusion for signs and symptoms of CRS and neurologic toxicities. In some embodiments, patients are monitored at least daily for 3, 4, 5, 6, 7, 8, 9, 10, 11, 12, 13, or 14 days.

In some embodiments, patients are instructed to remain within proximity of the certified healthcare facility for at least 4 weeks following infusion. In some embodiments, patients are instructed to remain within proximity of the certified healthcare facility for at least 1, 2, 3, 4, 5, 6, 7, 8, 9, or 10 weeks following infusion.

Clinical Trial

Figure 2:
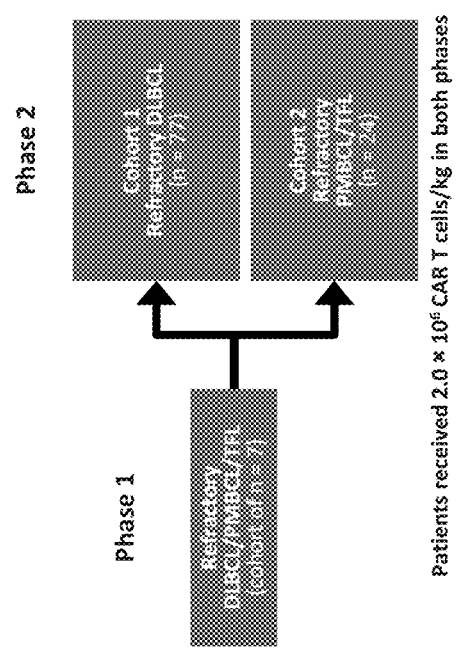
FIG. 2 shows a schematic representation of the ZUMA-1 clinical trial of patients receiving axicabtagene ciloleucel. AE, adverse event; axi-cel, axicabtagene ciloleucel; CAR, chimeric antigen receptor; CR, complete response; CRS, cytokine release syndrome; DLBCL, diffuse large B cell lymphoma; NE, neurologic event; ORR, objective response rate; PMBCL, primary mediastinal B cell lymphoma; TFL, transformed follicular lymphoma.

ZUMA-1 (NCT02348216) is a Phase 1/2, multicenter, pivotal study of axicabtagene ciloleucel (axi-cel) in patients with refractory aggressive large B cell lymphoma (FIG. 2) (Neelapu S N, Locke L F, et al. N Engl J Med. 2017; 377:2531-2544). Axicabtagene ciloleucel (axi-cel) Maintained Ongoing Responses at Median Follow-up of 15.4 Months. Of 108 patients with refractory large B cell lymphoma treated with axicabtagene ciloleucel (axi-cel) in ZUMA-1 with median follow-up of 15.4 months, 82% exhibited objective response rate (ORR), 58% complete response (CR) and ongoing responses were 42% including 40% CR. Cytokine release syndrome (CRS) and neurologic events (NE) were reversible (13% Grade≥3 CRS, 28% Grade≥3 NE: 3 Grade 5 adverse events.

Management of Severe Adverse Reactions

In some embodiments, the method comprises management of adverse reactions. In some embodiments, the adverse reaction is selected from the group consisting of cytokine release syndrome (CRS), a neurologic toxicity, a hypersensitivity reaction, a serious infection, a cytopenia and hypogammaglobulinemia.

In some embodiments, the signs and symptoms of adverse reactions are selected from the group consisting of fever, hypotension, tachycardia, hypoxia, and chills, include cardiac arrhythmias (including atrial fibrillation and ventricular tachycardia), cardiac arrest, cardiac failure, renal insufficiency, capillary leak syndrome, hypotension, hypoxia, organ toxicity, hemophagocytic lymphohistiocytosis/macrophage activation syndrome (HLH/MAS), seizure, encephalopathy, headache, tremor, dizziness, aphasia, delirium, insomnia anxiety, anaphylaxis, febrile neutropenia, thrombocytopenia, neutropenia, and anemia.

Cytokine Release Syndrome

In some embodiments, the method comprises identifying CRS based on clinical presentation. In some embodiments, the method comprises evaluating for and treating other causes of fever, hypoxia, and hypotension. Patients who experience≥Grade 2 CRS (e.g., hypotension, not responsive to fluids, or hypoxia requiring supplemental oxygenation) should be monitored with continuous cardiac telemetry and pulse oximetry. In some embodiments, for patients experiencing severe CRS, consider performing an echocardiogram to assess cardiac function. For severe or life-threatening CRS, intensive care supportive therapy may be considered.

In some embodiments, the method comprises monitoring patients at least daily for 7 days at the certified healthcare facility following infusion for signs and symptoms of CRS. In some embodiments, the method comprises monitoring patients for signs or symptoms of CRS for 4 weeks after infusion. In some embodiments, the method comprises counseling patients to seek immediate medical attention should signs or symptoms of CRS occur at any time. In some embodiments, the method comprises instituting treatment with supportive care, tocilizumab or tocilizumab and corticosteroids as indicated at the first sign of CRS.

Neurologic Toxicity

In some embodiments, the method comprises monitoring patients for signs and symptoms of neurologic toxicities. In some embodiments, the method comprises ruling out other causes of neurologic symptoms. Patients who experience≥Grade 2 neurologic toxicities should be monitored with continuous cardiac telemetry and pulse oximetry. Provide intensive care supportive therapy for severe or life threatening neurologic toxicities.

In some embodiments, the method comprises monitoring patients at least daily for 7 days at the certified healthcare facility following infusion for signs and symptoms of neurologic toxicities. In some embodiments, the method comprises monitoring patients for signs or symptoms of neurologic toxicities for 4 weeks after infusion.

Secondary Malignancies

In some embodiments, patients treated with CD19-directed genetically modified autologous T cell immunotherapy may develop secondary malignancies. In some embodiments, the method comprises monitoring life-long for secondary malignancies.

All publications, patents, and patent applications mentioned in this specification are herein incorporated by reference to the same extent as if each individual publication, patent, or patent application was specifically and individually indicated to be incorporated by reference. However, the citation of a reference herein should not be construed as an acknowledgement that such reference is prior art to the present invention. To the extent that any of the definitions or terms provided in the references incorporated by reference differ from the terms and discussion provided herein, the present terms and definitions control.

Additional Embodiments

One aspect of the present disclosure relates to methods of treating malignancy comprising measuring immune-related gene expression and/or T cell density at one or more site(s) of malignancy (i.e., the tumor microenvironment) prior to administration (e.g., at least one infusion) of CAR-T cells or T cells expressing an exogenous TCR. In some embodiments, said measurement is performed prior to chemotherapeutic conditioning and engineered T cell (e.g., CAR-T cell) administration.

In some embodiments, said measurement comprises determining a composite immune score based on immune-related gene expression, such as an ImmunoSign®21 or Immunosign®15 score. In some embodiments, said measurement comprises determining an immune score based on intratumoral density of T cells, including CD3+ and/or CD8+ T cells, such as Immunoscore®. In some embodiments, said measurement further comprises determining and assigning relative score(s), such as High or Low, based on comparison of a subject's immune score(s) to a predetermined threshold. In some embodiments, such predetermined threshold is or has been determined to have prognostic value with respect to the treatment of the malignancy with the engineered T cell.

In some embodiments, the disclosed methods further comprise a step of treatment optimization based on said measurement(s). For example, in some embodiments, the dose and/or schedule of engineered T cell (e.g., CAR-T cell) administration is optimized based on the immune score(s) of the tumor microenvironment. In exemplary embodiments, a subject with a low immune score, such as a low ImmunoSign®21 score, is administered a higher dose of CAR-T cells than a subject with a High immune score. In some embodiments, a subject with a low immune score is administered a dose that is about 25% higher, or about 50% higher, or about 100% higher, than a subject with a high immune score.

In additional and alternative exemplary embodiments, a subject with a Low immune score receives one or more additional CAR-T cell infusions. In some embodiments, a subject with a Low pretreatment immune score is administered a first dose of CAR-T cells, treatment response is assessed, and, if incomplete response is observed, an additional TME immune score measurement step is conducted. In some embodiments, an additional administration of CAR-T cells is performed if the subject's immune score is high following the first administration.

In some embodiments, the disclosed methods additionally or alternatively comprise a 'pre-treatment' step in which subjects with a low immune score are treated with the objective of improving their immune score prior to CAR-T administration. For example, in some embodiments, a patient with a Low immune score is administered one or more immunostimulants, such as cytokines, chemokines, or immune checkpoint inhibitors. In some embodiments, an additional measurement of immune score is performed prior to treatment.

In some embodiments, the prognostic value of a High immune score with respect to complete response based on CAR-T therapy is considered when evaluating treatment options. For example, in some embodiments, a subject with a high immune score receives CAR-T administration as an earlier line of therapy than a subject with a low immune score.

The present invention is further illustrated by the following examples, which should not be construed as further limiting. The contents of all references cited throughout this application are expressly incorporated herein by reference.

EXAMPLES

Example 1: Baseline TME Immune Gene Expression as Prognostic of Axi-Cel Response Axicabtagene ciloleucel (axi-cel; YESCARTA®) is an autologous anti-CD19 chimeric antigen receptor (CAR) T cell therapy currently approved by the US FDA and EMA for the treatment of patients with relapsed or refractory large B cell lymphoma with 2 or more prior systemic therapies. The structure of the axi-cel CAR is depicted schematically in FIG. 1.

ZUMA-1 (NCT02348216) is a Phase 1/2, multicenter, pivotal study of axicabtagene ciloleucel (axi-cel) in patients with refractory aggressive large B cell lymphoma (Neelapu S N, Locke L F, et al. N Engl J Med. 2017; 377:2531-2544). ZUMA-1 phases and cohorts sizes are depicted schematically in FIG. 2. Patients received $2.0 \times 10^6$ CAR T cells/kg in both phases.

Of 108 patients with refractory large B cell lymphoma treated with axicabtagene ciloleucel (axi-cel) in ZUMA-1, the overall response rate was 82%, and the complete response (CR) rate was 58%. Cytokine release syndrome (CRS) and neurologic events (NE) were mostly reversible (11% Grade≥3 CRS; 32% Grade≥3 NE; 4 Grade 5 adverse events (including 2 non-axi-cel related events)). At Median Follow-Up of 15.4 months, ongoing response rate was 42%, including 40% CR. At Median Follow-Up of 27.1 months, the ongoing response rate was 39%, including 37% CR.

A post-hoc analysis of Phase 2 of ZUMA-1 was designed to explore the association of key pre-treatment features of the tumor immune microenvironment (TME). Baseline biopsies were analyzed from 25 patients treated with axicabtagene ciloleucel (axi-cel) with a minimum follow-up of 9 months. Table 1 shows patient and tumor baseline characteristics and treatment results.

TABLE 1

Patient and Tumor Baseline Characteristics and Treatment

| | Current Gene Expression Study (n = 25) | ZUMA-1 Overall (N = 101) |
|---|---|---|
| Baseline characteristics | | |
| Tumor histology, n (%) | | |
| DLBCL | 21 (84) | 77 (76) |
| PMBCL/TFL | 4 (16) | 24 (24) |
| IPI score 3-4, n (%) | 11 (44) | 48 (48) |
| ≥3 Prior lines of therapy, n (%) | 18 (72) | 70 (69) |
| Treatment results | | |
| Median CAR peak levels, cells/µL (range) | 36 (1-1514) | 38 (1-1514) |

CAR, chimeric antigen receptor;
DLBCL, diffuse large B cell lymphoma;
IPI, International Prognostic Index;
ORR, objective response rate,
PMBCL, primary mediastinal B cell lymphoma,
TFL, transformed follicular lymphoma.

The objective response rate in these 25 patients was 80% with 20 responders and 5 nonresponders. In a subsequent data cutoff (minimum of 12 months of follow up), one patient subsequently converted from a "nonresponder" to "responder" at Month 1.

Figure 3:
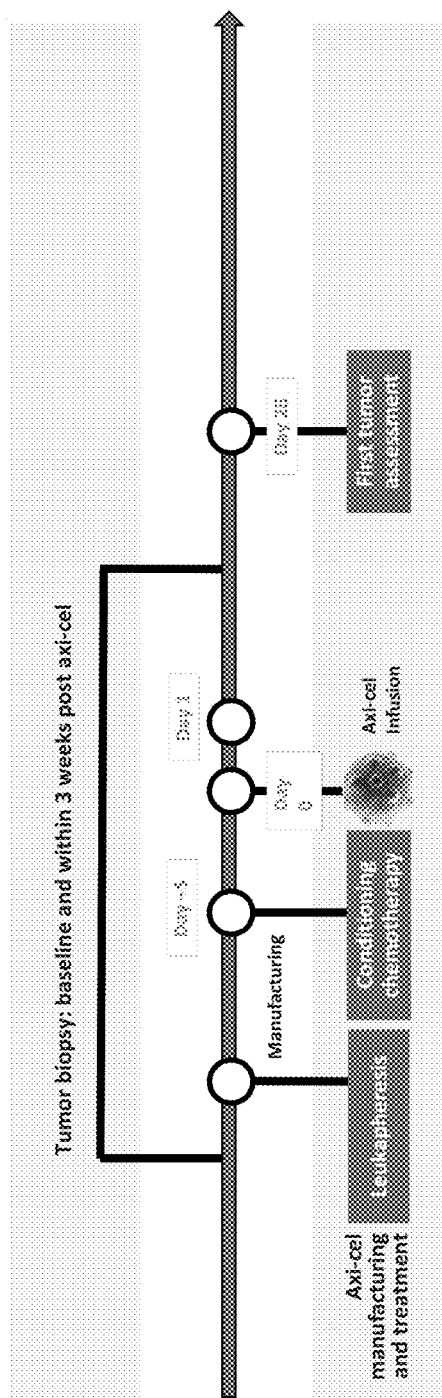
FIG. 3 shows a schematic representation of the ZUMA-1 clinical trial protocol and timing of paired biopsies.
Figure 4:
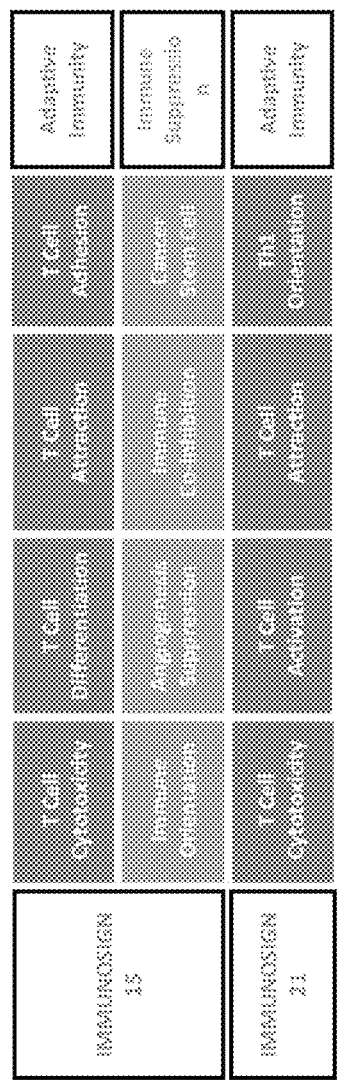
FIG. 4 shows Immunosign® clinical research assay panel used to evaluate key immune pathways within the tumor microenvironment.
Figure 6:
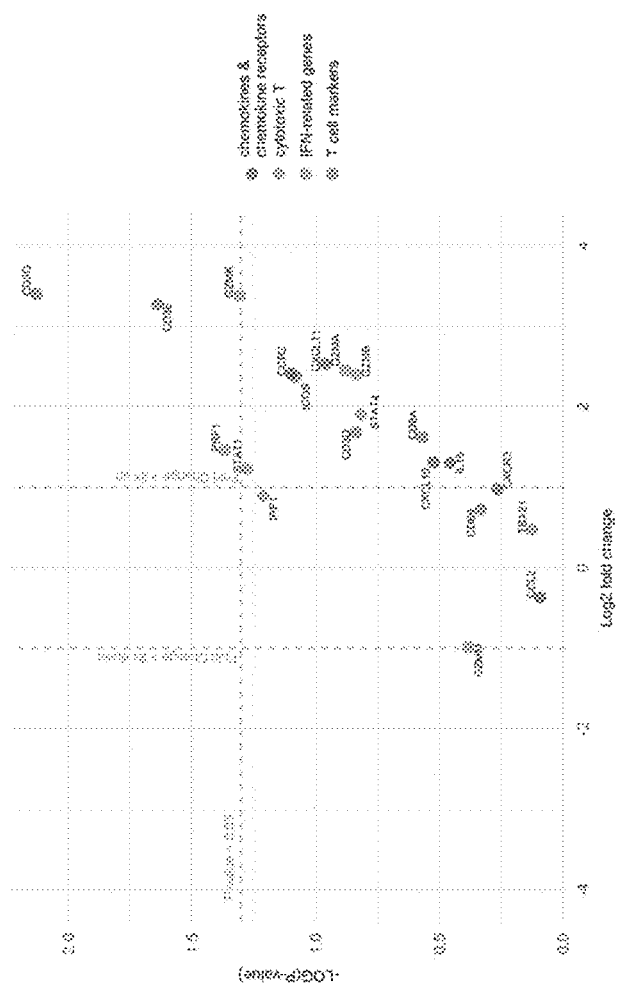
FIG. 6 shows differences in expression of Immunosign®21 genes in responders compared to nonresponders performed on samples from 25 patients treated with axicabtagene ciloleucel (axi-cel) with a minimum follow-up of 9 months.
Figure 7A:
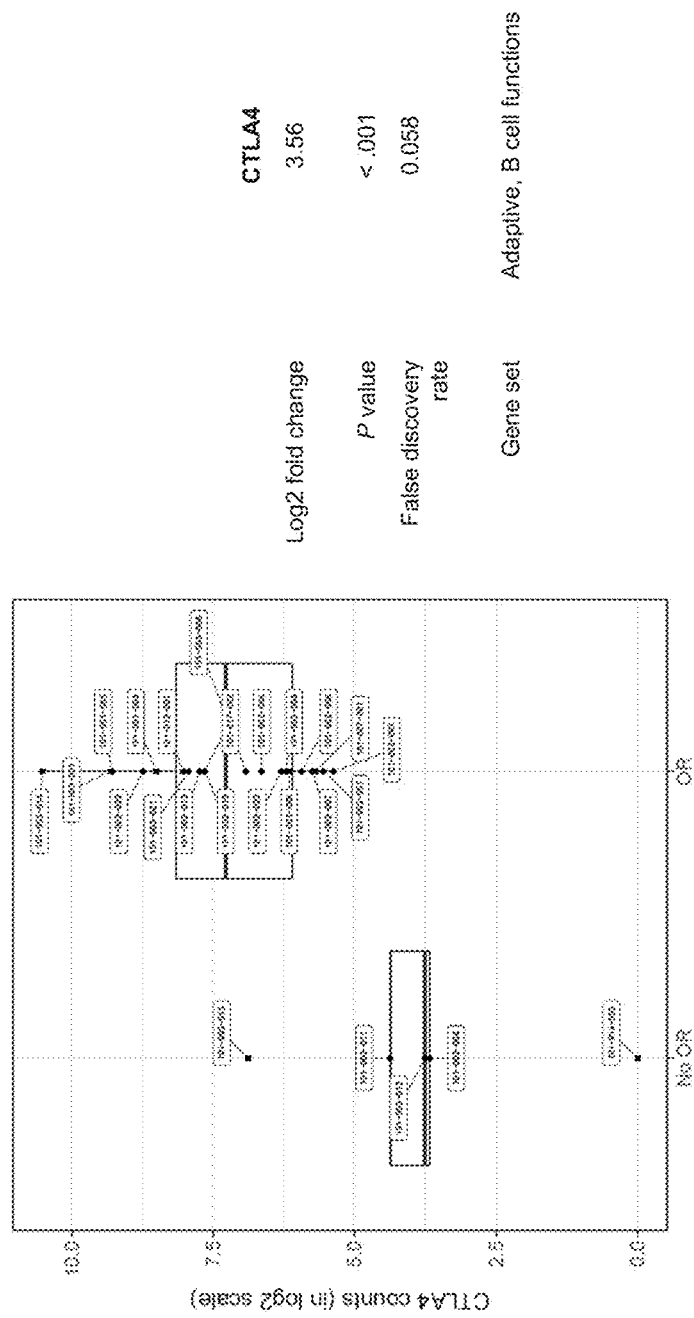
FIGS. 7A-7C show association of the top three immune environment genes, CTLA4 (FIG. 7A), CD3γ (FIG. 7B), and CD3c (FIG. 7C), which are elevated in tumors from responders from a prespecified 43 immune gene panel performed on samples from 25 patients treated with axicabtagene ciloleucel (axi-cel) with a minimum follow-up of 9 months.
Figure 7B:
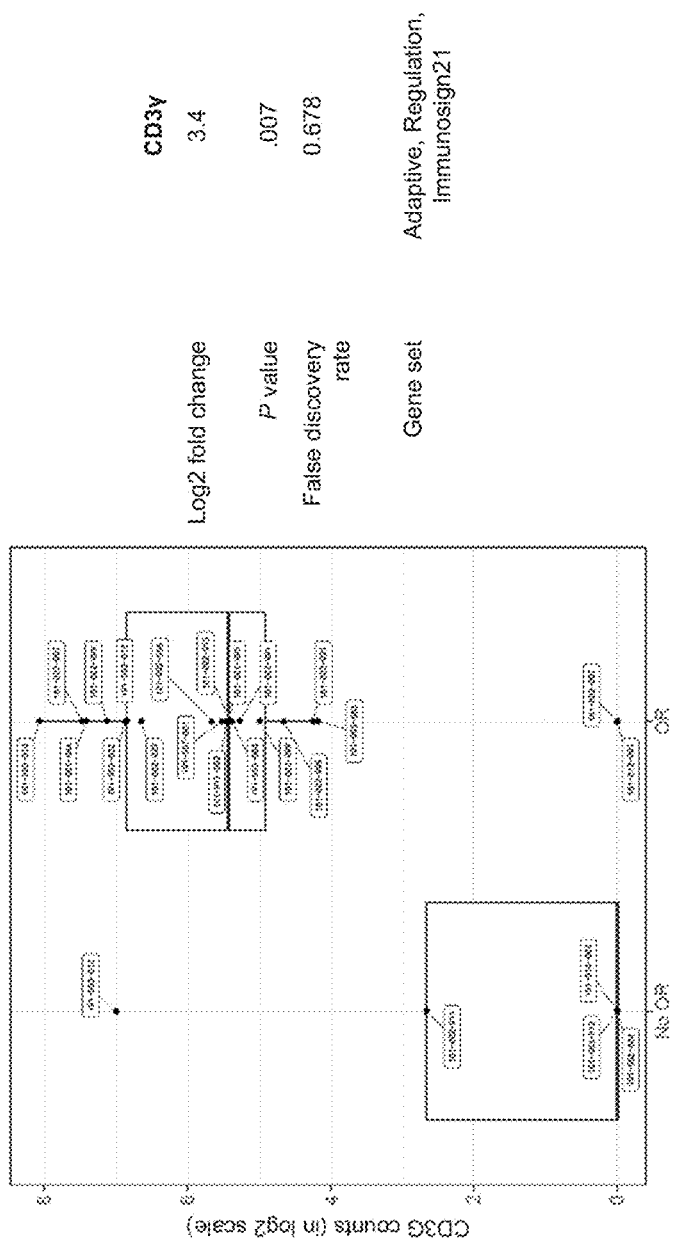
Figure 7C:
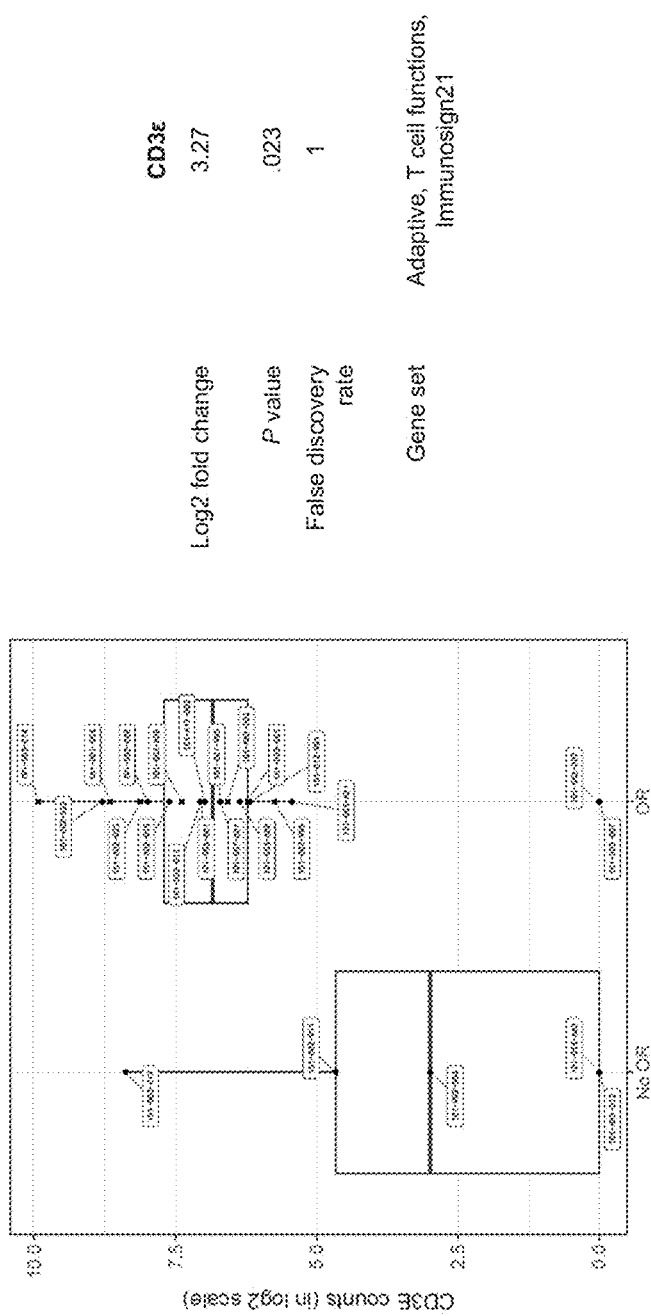

Tumor biopsies were taken at baseline and within three weeks post axicabtagene ciloleucel (axi-cel) administration as shown in FIG. 3. Baseline fresh frozen core biopsies were analyzed with the Immunosign® Clinical Research assay using nCounter® technology (NanoString) to measure the gene expression level of multiple immune genes in a multiplex format. The assay was further developed for utilizing minimal amounts of RNA from fresh frozen or formalin fixed tumor tissue. A prespecified bioinformatics method and cutoffs were applied to immune-mediated tumor regression genes to assess adaptive immunity including T cell cytotoxicity, T cell differentiation, T cell attraction, T cell adhesion and immune suppression including immune orientation, angiogenesis suppression, immune co-inhibition, and cancer stem cells. (Immunosign®; FIG. 4; Galon J, et al. Immunity. 2013; 39:11-26; www.haliodx.com/clinical-research-services/immunosignr/). The bioinformatics method included T cell-specific (effector T cell, Th1) genes, interferon pathway-related genes, chemokines, and immune checkpoints. The high/low Immunosign®21 score cut-off was defined as the 25th percentile of the observed scores among samples. High score indicates expression of immune-related genes potentially associated with tumor response.

Expression analysis and scoring were used to examine associations between TME features and response. A broader analysis using prespecified gene sets was also applied as shown in Table 2. A prespecified 43 gene set consisting of the Immusign®15, Immunosign®21, and other genes and all 763 genes from the PanCancer Immune Profiling Panel were included. (nCounter PanCancer Immune Profiling Panel. https://www.nanostring.com/products/gene-expression-panels/hallmarks-cancer-gene-expression-panel-collection/pan-cancer-immune-profiling-panel). Fisher's exact test and Wilcoxon signed rank test with multiple test correction by false discovery rate (Benjamini-Hochberg) were used.

TABLE 2

Prespecified Gene Sets

| Immunosign ®21 | | Expanded 43 Immune Gene Panel | | | | PanCancer Immune Profiling Panel (763 genes) | |
|---|---|---|---|---|---|---|---|
| CD3G | STAT4 | CTLA4 | GZMH | CD8A | PDCD1 | B cells | T cells |
| CD3E | CD3D | CD3G | IRF1 | CX3CL1 | TNFRSF9 | e.g., BLK, | e.g., CD2, CD2E, |
| GZMK | GZMM | CD3E | GZMA | CXCL10 | TSLP | CD19, CR2, | CD3G, CD6 |
| PRF1 | CD8A | REN | GZMB | TNFRSF18 | CCL2 | MS4A1, | |
| ICOS | CXCL10 | GZMK | CXCL11 | CD69 | CD247 | TNFRSF17 | |
| STAT1 | IL15 | CCL5 | STAT4 | CD274 | GNLY | Innate immune response | |
| CCR2 | CCL2 | ITGAE | LAG3 | IL15 | LTK | Cytotoxic cells | Dendritic cells |
| IRF1 | TBX21 | PRF1 | CD3D | PF4 | TBX21 | e.g., CD8, BLC2 | e.g., CCL12, CCL17 |
| GZMA | CXCR3 | ICOS | CXCL9 | IFNG | VEGFA | Macrophages | Granulocytes |
| GZMB | CD69 | STAT1 | GZMM | CXCL13 | CXCR3 | e.g., APOE, CCL7 | e.g., CMA1, CSF3R |
| CXCL11 | | CCR2 | IL17A | PROM1 | | | |

Pre-existing immune features of the tumor microenvironment (TME) are associated with a response to axicabtagene ciloleucel (axi-cel). As shown in FIG. 5A, TME Immunosign®21 score at baseline was elevated in responders compared to nonresponders, with a clinical follow up of ≥9 months (P=0.012). 85% (17/20) of responders had high Immunosign®21 scores and 80% (4/5) of nonresponders had low Immunosign®21 scores (FIGS. 5B and 5C). In a sensitivity analysis including a patient with delayed response at 12 months, association between Immunosign®21 and response had a P=0.053.

Top immune-related genes upregulated in TME at baseline in responders vs nonresponders included CTLA4, CD3g, CD3e, CD27, SH2B2, and ICOSL. Expression of other genes was relatively decreased in TME at baseline in responders compared to nonresponders including, MHC class II genes and cancer testes antigens PRAME, MAGE, SSX. The association with MHC class II genes is surprising in light of the positive prognostic value of MHC class II expression in diffuse large B cell lymphoma (Rimsza L M, et al. *Blood.* 2004; 103:4251-4258. Additional genes differentially expressed in TME in Responders compared to nonresponders from an expanded 763 gene PanCancer Immune Profiling Panel is shown in Table 3.

TABLE 3

Differentially Expressed genes in TME in Responders vs. Nonresponders

| Gene | Log2 fold change | P value | False discovery rate | Gene sets |
|---|---|---|---|---|
| Upregulated in Responders vs Nonresponders | | | | |
| CD27 | 2.46 | .039 | 1 | Immune co-receptor |
| SH2B2 | 1.84 | <.001 | 1 | Regulation |
| ICOSLG | 1.54 | .035 | 1 | Immune co-receptor |
| Down-Regulated in Responders vs Nonresponders | | | | |
| HLA-DQA1 | −7.85 | .038 | 1 | Adaptive, Antigen Processing |
| HLA-DQB1 | −7.05 | .017 | 1 | Adaptive, Antigen Processing |
| MAGEB2 | −6.26 | .007 | 1 | Cancer Testes |
| PRAME | −5.11 | .015 | 1 | Cancer Testes |
| MAGEA1 | −3.89 | .028 | 1 | Cancer Testes |
| IL22RA1 | −3.48 | .002 | 1 | Chemokines |
| SSX1 | −3.18 | .001 | 1 | Cancer Testes |
| CCL20 | −3.13 | .044 | 1 | Chemokines |
| NEFL | −3.1 | .002 | 1 | Cell Functions |
| C9 | −2.87 | .028 | 1 | Innate, Complement |
| GZMM | −2.83 | .040 | 1 | Innate, ImmunoSign®21 |
| KIR Act Subgroup 2 | −2.66 | .004 | 1 | Innate immunity |
| HLA-DOB | −2.12 | .043 | 1 | Adaptive, Antigen Processing |

Example 2: Baseline Intratumoral T Cell Density as Prognostic of Axi-Cel Response An additional post-hoc analysis of Phase 2 of ZUMA-1 was designed to explore the association of key pre-treatment features of the tumor immune microenvironment (TME)—in particular, CD3+ and CD8+ T cell densities and Immunoscore®—with response to axi-cel and immune gene expression (including Immunosign® 21).

Pre-conditioning tissue biopsies were formalin-fixed and paraffin-embedded (FFPE) for analysis by immunohistochemistry for density of CD3+ and CD8+ T cells (cells/mm2). CD3 and CD8 staining was performed using Benchmark® XT station on 2 consecutive FFPE slices (4 µm). Positive cell staining density was determined with dedicated digital pathology software.

The Immunoscore® assay measures the density of CD8+ cytotoxic T cells and CD3+ T cells of resected or biopsied cancer samples and is performed on formalin-fixed paraffin-embedded tissue slides. Pretreatment (before chemotherapeutic conditioning) tumor tissue biopsies were analyzed by immunohistochemistry for density (cells/mm$^2$) of T cell subsets (CD3+, CD8+). CD3 and CD8 staining was performed using a Benchmark® XT station on 2 consecutive FFPE slices (4 µm). Measurement of positive cell area was conducted using dedicated digital pathology software. For each subject, CD3 and CD8 immunohistochemical staining for the 25 baseline biopsy samples was scored and converted into an ImmunoScore® (a numerical index of T cell density) with the HalioDx algorithm and analysis cutoffs as described in Galon et al., *J Pathol.* 232:199-209 (2014). The median of observed scores was defined as the threshold of high and low Immunoscore®, with high Immunoscore representing relatively increased intratumoral T cell infiltration. Welch's t-test was used to compare Immunoscore®, CD3, and CD8 levels among subjects with CR against subjects with partial response, stable disease, and progressive disease.

Results: A majority of patients with higher densities of intra-tumoral CD3+ and CD8+ T cells, and high Immunoscore®, all determined pre-treatment, achieved CR (FIGS. 8A-8C). Overall, higher pretreatment Immunoscore® was associated with achievement of CR (P=0.048; FIGS. 8A and 8B). Pretreatment intratumoral densities of CD3+ and CD8+ T cells were positively associated with achievement of CR (P=0.025 and 0.049; FIGS. 9A and 9B, respectively). Patients who did not achieve CR showed predominantly low densities of intra-tumoral CD3+ and CD8+ T cells, and low Immunoscore®. (FIGS. 8A and 8C).

Figure 10:
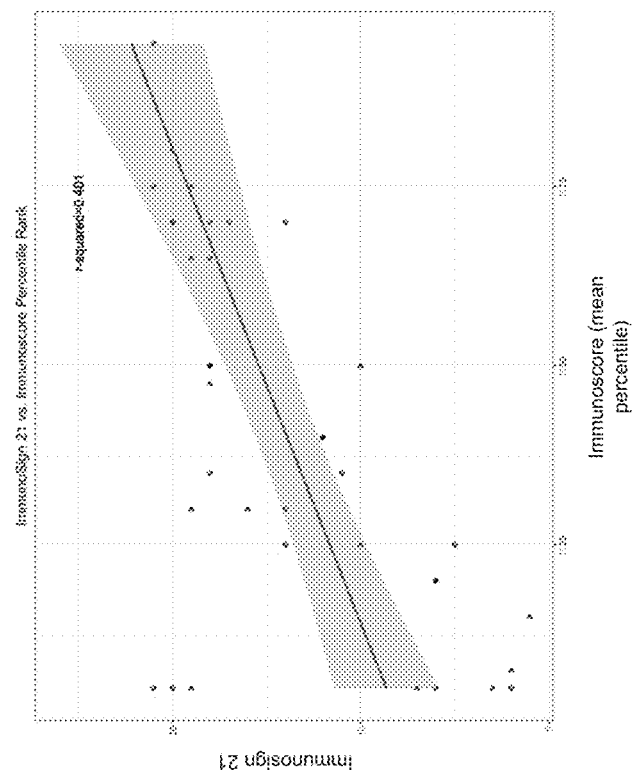
FIG. 10 plots the correlation between Immunosign®21 score and Immunoscore® as evaluated from baseline biopsies from treated patients.

Immunoscore® and Immunosign® 21 evaluated pre-treatment in the same tumor biopsies demonstrated 82% concordance (95% CI, 65-93; $r^2$=0.451; FIG. 10), suggesting a potential relationship between higher density of T cell infiltrate and a permissive gene signature.

The findings from Example 1 and Example 2 point to a key role of the pretreatment TME in the response to CAR T cell therapy. Anti-CD19 CAR T therapy may overcome the poor prognosis associated with a low Immunosign®21 score or Immunoscore®.

Example 3: Tumor Immune Microenvironment

Figure 11:
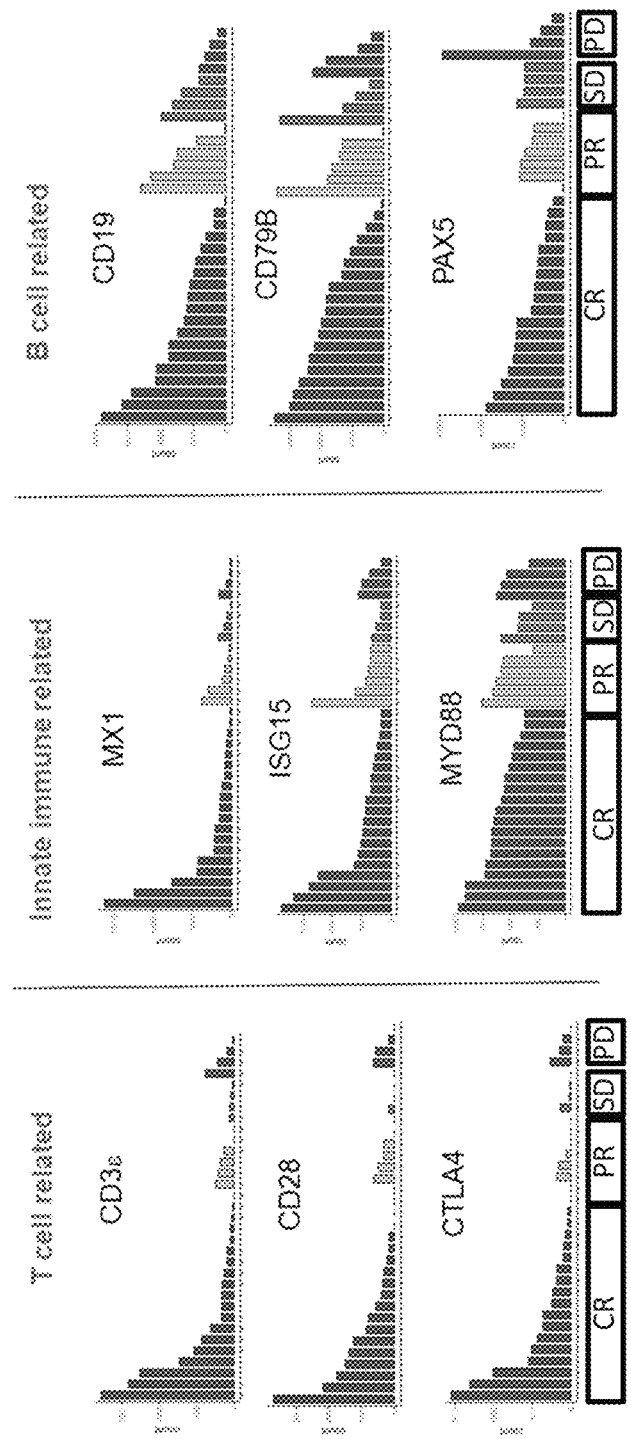
FIG. 11 shows pre-treatment gene expression analysis in the TME of T cell related genes (CD3c, CD28, and CTLA4), innate immune related genes (MX1, ISG15, and MYD88) and B cell related genes (CD19, CD79B, and PAX5) and clinical outcome at 1 year follow up of axi-cel treatment. CR: complete response; PR: partial response; SD: stable disease; PD: progressive disease.

Further analysis of patient samples showed that CAR T cell expansion occurred within 2 weeks of treatment and was accompanied by elevation of cytokines in the immune programs. Pharmacodynamic profiling showed rapid increase above baseline in proliferative markers (IL-15 and IL-2), inflammatory markers (IL-6, CRP, SAA, IL-5, Ferritin, IL-1Ra, IL-2Ra), immune modulating markers (GM-CSF, IFN-γ, IL-10), chemokines (IL-8, IP-10, MCP-1) and effector markers (Granzyme B). Gene expression analysis suggests that pre-treatment T cell related genes (CD3c, CD28, and CTLA4), innate immune related genes (MX1, ISG15, and MYD88) and B cell related genes (CD19, CD79B, and PAX5) may have correlated with clinical outcome (FIG. 11).

Figure 12:
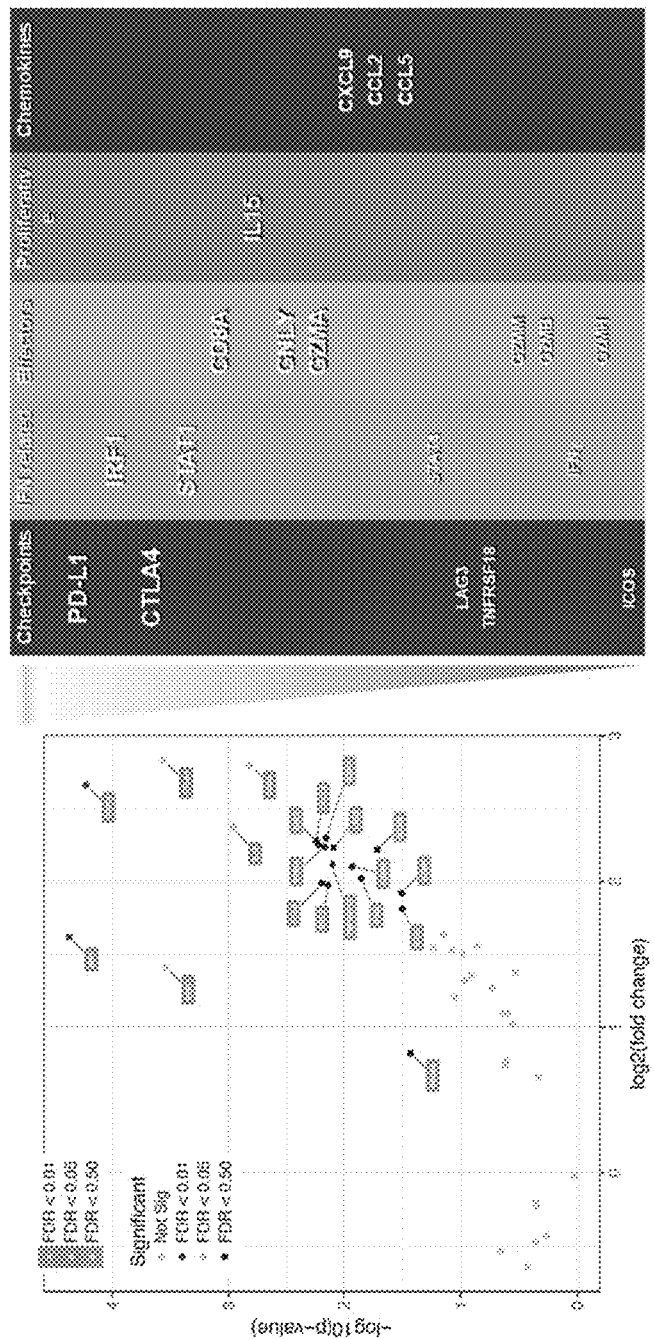
FIG. 12 shows fold change in TME gene expression 7-21 days after CAR-T treatment indicating relative change compared to baseline in immune inhibiting checkpoints (PD-L1, CTLA4, LAG3, TNFRSF18, ICOS), IFN-related genes (IRF1, STAT1, STAT4, IFNγ) and chemokines (CXCL9, CCL2, CCL5), effectors (CD8A, GNLY, GZMA, GZMM, GZMB, GZMH) and proliferative marker IL-15.
Figure 13A:
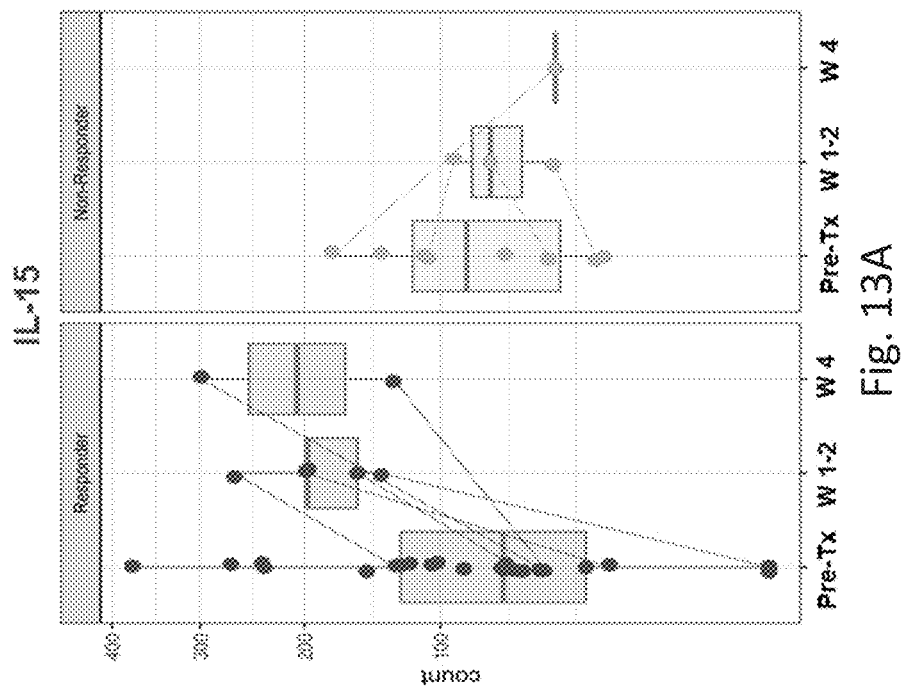
FIGS. 13A and 13B show nanostring analysis of differential changes in IL-15 (FIG. 13A) and PD-L1 (FIG. 13B). Pre-Tx: pre-treatment; W1-2: week 1-2; W4: week 4.
Figure 13B:
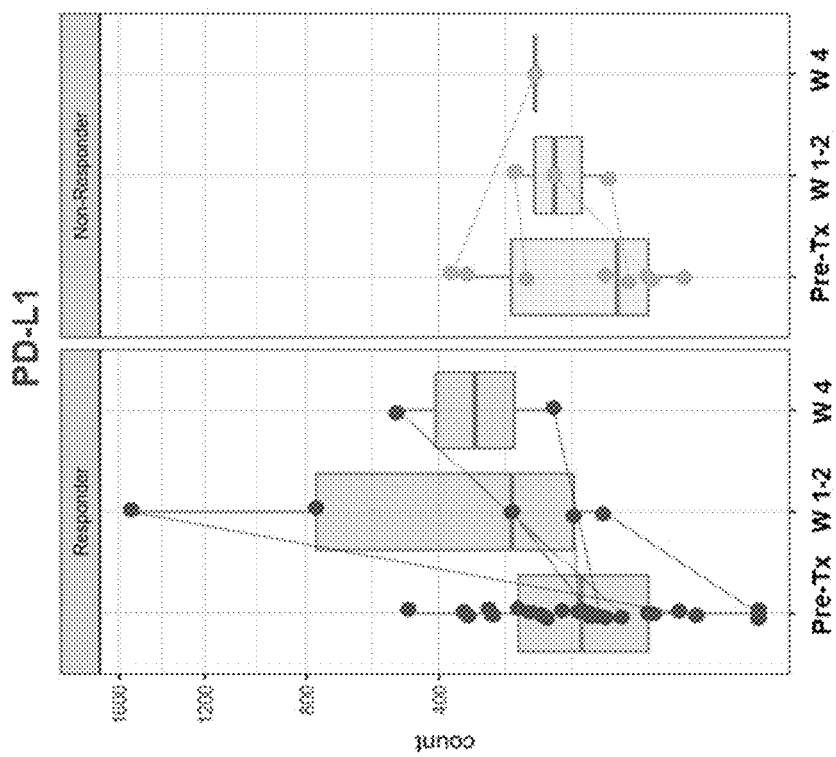

CAR T cells were detected in TME in Zuma-1 patients (7-21 days post treatment) using in-situ hybridization (ISH) for CAR T RNA and immunohistochemistry (IHC) with antibodies that recognize separate CAR epitopes described in International Patent Application Publication Nos. WO2018/013563A1 and WO2018/053790A1. Increased rates of ongoing response at 1 year were observed in patients with reduced pre-treatment tumor burden. These data suggest that CAR T cell engraftment commensurate with tumor burden may overcome large tumors. CAR T cell treatment was associated with changes in the TME. Analysis of transcripts from a pre-specified 43 immune gene panel showed upregulation in tumors 7-21 days after treatment. Increases in immune inhibiting checkpoints (PD-L1, CTLA4, LAG3, TNFRSF18, ICOS), IFN-related genes (IRF1, STAT1, STAT4, IFNγ) and chemokines (CXCL9, CCL2, CCL5), effectors (CD8A, GNLY, GZMA, GZMM, GZMB, GZMH) and proliferative marker IL-15 were observed in response to treatment (FIG. 12). Nanostring analysis showed elevation of IL-15 and PD-L1 gene expression in subjects with complete or partial response (FIGS. 13A and 13B).

Biopsies from patients with Large Cell Lymphoma and B cell Acute Lymphoblastic Leukemia (B-ALL) were evaluated for CD19 and PD-L1 expression. At least ⅓rd of subjects who relapse post Axi-cel had tumors negative for CD19 expression. Analysis of B cell and immune-related molecules at progression, identified relapse with CD19+ or CD19− Tumor Cells. At Baseline, 94% (16/17) of evaluable patients were CD19+. Post-progression tumor biopsies from 21 evaluable patients showed 33% were CD19− and 62% were PD-L1+.

What is claimed:

1. A method of treating a malignancy in a patient comprising:
   (a) analyzing a tumor biopsy from the patient to characterize the tumor microenvironment; and
   (b) administering an effective dose of anti-CD19 chimeric antigen receptor (CAR)-T cells to the patient, wherein the effective dose is determined using the characteristics of the tumor microenvironment, wherein the characteristics of the tumor microenvironment comprise gene expression profiling,
   wherein the gene expression profiling comprises determining the expression level of a specified panel of genes in a solid tumor using RNA extracted from intact fresh frozen or formalin fixed tumor tissue as opposed to extracted from isolated cells, wherein the specified panel of genes consists of two or more genes selected from CTLA4, CD3g, CD3e, CD27, SH2B2, ICOSL, MHC class II genes, and cancer testes antigens PRAME, MAGE, SSX, wherein at least one gene is not a T-cell marker, and combinations thereof.

2. The method of claim 1, further comprising determining an immune score based on the gene expression profile.

3. The method of claim 2, further comprising modulating the total dose using the immune score.

4. The method of claim 1, wherein the effective dose comprises at least $1\times10^6$ CAR-positive viable T cells per kg body weight.

5. The method of claim 1, wherein the malignancy is a solid tumor, sarcoma, carcinoma, lymphoma, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), chronic or acute leukemia, acute myeloid leukemia, chronic myeloid leukemia, acute lymphoblastic leukemia (ALL) (including non T cell ALL), chronic lymphocytic leukemia (CLL), T-cell lymphoma, one or more of B-cell acute lymphoid leukemia ("BALL"), T-cell acute lymphoid leukemia ("TALL"), acute lymphoid leukemia (ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, myelodysplasia and myelodysplastic syndrome, plasmablastic lymphoma, plasmacytoid dendritic cell neoplasm, Waldenstrom macroglobulinemia, a plasma cell proliferative disorder (e.g., asymptomatic myeloma (smoldering multiple myeloma or indolent myeloma), monoclonal gammapathy of undetermined significance (MGUS), plasmacytomas (e.g., plasma cell dyscrasia, solitary myeloma, solitary plasmacytoma, extramedullary plasmacytoma, and multiple plasmacytoma), systemic amyloid light chain amyloidosis, POEMS syndrome (also known as Crow-Fukase syndrome, Takatsuki disease, and PEP syndrome), or a combination thereof.

6. The method of claim 1, wherein the effective dose is optimized to increase likelihood of the patient responding to anti-CD19 CAR-T treatment.

* * * * *